(12) United States Patent
Graus et al.

(10) Patent No.: US 7,572,897 B2
(45) Date of Patent: Aug. 11, 2009

(54) ANTIBODIES AGAINST INSULIN-LIKE GROWTH FACTOR I RECEPTOR AND USES THEREOF

(75) Inventors: Yvo Graus, Ede (NL); Erhard Kopetzki, Penzberg (DE); Klaus-Peter Kuenkele, Benediktbeuern (DE); Olaf Mundigl, Weilheim (DE); Paul Parren, Odijk (NL); Frank Rebers, Utrecht (NL); Ralf Schumacher, Penzberg (DE); Jan van de Winkel, Zeist (NL); Martine Vriesema-van Vugt, Houten (NL)

(73) Assignee: Hoffman-La Roche Inc., Nutley, NJ (US)

( * ) Notice: Subject to any disclaimer, the term of this patent is extended or adjusted under 35 U.S.C. 154(b) by 121 days.

(21) Appl. No.: 11/869,250

(22) Filed: Oct. 9, 2007

(65) Prior Publication Data

US 2008/0132686 A1 Jun. 5, 2008

Related U.S. Application Data

(62) Division of application No. 10/886,838, filed on Jul. 8, 2004.

(30) Foreign Application Priority Data

Jul. 10, 2003 (EP) .................................. 03015526

(51) Int. Cl.
*C07K 16/28* (2006.01)
(52) U.S. Cl. ............................ 530/388.15; 530/388.22; 530/388.8
(58) Field of Classification Search ........................ None
See application file for complete search history.

(56) References Cited

U.S. PATENT DOCUMENTS 5,770,429 A 6/1998 Lonberg et al.

FOREIGN PATENT DOCUMENTS

| WO | WO 87/05330 | 9/1987 |
| WO | WO 95/14930 A1 | 6/1995 |
| WO | WO 01/14424 | 3/2001 |
| WO | WO 02/053596 A2 | 7/2002 |
| WO | WO 03/059951 A2 | 7/2003 |
| WO | WO 03/100008 A2 | 12/2003 |
| WO | WO 2004/071529 | 8/2004 |

OTHER PUBLICATIONS

Adams, T.E. et al, Cell. Mol. Life Sci. 57 (2000) 1060-1063.
Brüggemann, M. et al, J. Exp. Med. 166 (1987) 1351-1361.
Chen, J. et al, EMBO J. 12 (1993) 821-830.
Fishwild, D.M. et al, Nat. Biotechnol. 14 (1996) 845-851.
Lonberg, N. et al, Nature 368 (1994) 856-859.
Love, T.W. et al, Methods Enzymol. 178 (1989) 515-527.
Pietrzkowski, Z. et al, Cell Growth Differ. 4 (1992) 199-205.
Riechmann, L. et al, Nature 332 (1988) 323-327.
Schlaeger, E.J. Cytotechnology 30 (1999) 71-83.
Wilman, "Prodrugs in Cancer Chemotherapy", Biochemical Society Transactions, 14, 375-383, 615th Meeting, Belfast (1986).
Rohlik Qtand al., Biochemical and Biophysical Research Communications, vol. 149, No. 1, pp. 276-281 (1987), XP008026319.
Li S-L et, Cancer Immunology and Immunotherapy, Berlin, DE, vol. 49, No. 4/5, pp. 243-252 (2000), XP001113064.
Li Shu-Lian et al, Cancer Immunol. Immunother., vol. 49, pp. 243-252 (2000), XP002267730.
Hailey J. et al, Molecular Cancer Therapeutics, vol. 1, pp. 1349-1353 (2002), XP008026465.
Pederson et al., Cellular Signalling, 17: 1343-1351 (2005).

*Primary Examiner*—Michail A Belyavskyi
*Assistant Examiner*—Zachary Skelding
(74) *Attorney, Agent, or Firm*—George W. Johnston; Patricia S. Rocha-Tramaloni; David E. Wildman

(57) ABSTRACT

Antibodies against insulin like growth factor I receptor (IGF-IR), methods for their production, pharmaceutical compositions containing said antibodies, and uses for such antibodies are disclosed. Antibodies against IGF-IR are implicated in antitumor therapy.

6 Claims, 13 Drawing Sheets

Fig. 12

| H322M xenograft | vehicle | 10 mg/kg | 2.5 mg/kg | 0.6 mg/kg | 0.15 mg/kg |
|---|---|---|---|---|---|
| IGF-IR | | | | | |

SEQUENCE LISTING

<160> NUMBER OF SEQ ID NOS: 8

<210> SEQ ID NO 1
<211> LENGTH: 118
<212> TYPE: PRT
<213> ORGANISM: Homo sapiens

<400> SEQUENCE: 1

Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 2
<211> LENGTH: 108
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 3
<211> LENGTH: 118
<212> TYPE: PRT
<213> ORGANISM: Homo sapiens

<400> SEQUENCE: 3

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Met
            35                  40                  45

Ala Ile Ile Trp Phe Asp Gly Ser Lys Tyr Tyr Gly Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Glu Leu Gly Arg Arg Tyr Phe Asp Leu Trp Gly Arg Gly Thr
                100                 105                 110

Leu Val Thr Val Ser Ser
        115

<210> SEQ ID NO 4
<211> LENGTH: 108
<212> TYPE: PRT
<213> ORGANISM: Homo sapiens

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ile Lys
            100                 105

<210> SEQ ID NO 5
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 5
```

-continued

| | | |
|---|---|---|
| gcc tcc acc aag ggc cca tcg gtc ttc ccc ctg gca ccc tcc tcc aag<br>Ala Ser Thr Lys Gly Pro Ser Val Phe Pro Leu Ala Pro Ser Ser Lys<br>1                        5                      10                 15 | 48 |
| agc acc tct ggg ggc aca gcg gcc ctg ggc tgc ctg gtc aag gac tac<br>Ser Thr Ser Gly Gly Thr Ala Ala Leu Gly Cys Leu Val Lys Asp Tyr<br>                20                      25                      30 | 96 |
| ttc ccc gaa ccg gtg acg gtg tcg tgg aac tca ggc gcc ctg acc agc<br>Phe Pro Glu Pro Val Thr Val Ser Trp Asn Ser Gly Ala Leu Thr Ser<br>                    35                       40                      45 | 144 |
| ggc gtg cac acc ttc ccg gct gtc cta cag tcc tca gga ctc tac tcc<br>Gly Val His Thr Phe Pro Ala Val Leu Gln Ser Ser Gly Leu Tyr Ser<br>        50                        55                      60 | 192 |
| ctc agc agc gtg gtg acc gtg ccc tcc agc agc ttg ggc acc cag acc<br>Leu Ser Ser Val Val Thr Val Pro Ser Ser Ser Leu Gly Thr Gln Thr<br>65                      70                      75                      80 | 240 |
| tac atc tgc aac gtg aat cac aag ccc agc aac acc aag gtg gac aag<br>Tyr Ile Cys Asn Val Asn His Lys Pro Ser Asn Thr Lys Val Asp Lys<br>                        85                      90                      95 | 288 |
| aaa gtt gag ccc aaa tct tgt gac aaa act cac aca tgc cca ccg tgc<br>Lys Val Glu Pro Lys Ser Cys Asp Lys Thr His Thr Cys Pro Pro Cys<br>                100                     105                   110 | 336 |
| cca gca cct gaa ctc ctg ggg gga ccg tca gtc ttc ctc ttc ccc cca<br>Pro Ala Pro Glu Leu Leu Gly Gly Pro Ser Val Phe Leu Phe Pro Pro<br>              115                     120                   125 | 384 |
| aaa ccc aag gac acc ctc atg atc tcc cgg acc cct gag gtc aca tgc<br>Lys Pro Lys Asp Thr Leu Met Ile Ser Arg Thr Pro Glu Val Thr Cys<br>130                      135                     140 | 432 |
| gtg gtg gtg gac gtg agc cac gaa gac cct gag gtc aag ttc aac tgg<br>Val Val Val Asp Val Ser His Glu Asp Pro Glu Val Lys Phe Asn Trp<br>145                      150                     155                   160 | 480 |
| tac gtg gac ggc gtg gag gtg cat aat gcc aag aca aag ccg cgg gag<br>Tyr Val Asp Gly Val Glu Val His Asn Ala Lys Thr Lys Pro Arg Glu<br>                  165                     170                   175 | 528 |
| gag cag tac aac agc acg tac cgt gtg gtc agc gtc ctc acc gtc ctg<br>Glu Gln Tyr Asn Ser Thr Tyr Arg Val Val Ser Val Leu Thr Val Leu<br>                180                     185                   190 | 576 |
| cac cag gac tgg ctg aat ggc aag gag tac aag tgc aag gtc tcc aac<br>His Gln Asp Trp Leu Asn Gly Lys Glu Tyr Lys Cys Lys Val Ser Asn<br>             195                     200                   205 | 624 |
| aaa gcc ctc cca gcc ccc atc gag aaa acc atc tcc aaa gcc aaa ggg<br>Lys Ala Leu Pro Ala Pro Ile Glu Lys Thr Ile Ser Lys Ala Lys Gly<br>210                      215                     220 | 672 |
| cag ccc cga gaa cca cag gtg tac acc ctg ccc cca tcc cgg gat gag<br>Gln Pro Arg Glu Pro Gln Val Tyr Thr Leu Pro Pro Ser Arg Asp Glu<br>225                      230                     235                   240 | 720 |
| ctg acc aag aac cag gtc agc ctg acc tgc ctg gtc aaa ggc ttc tat<br>Leu Thr Lys Asn Gln Val Ser Leu Thr Cys Leu Val Lys Gly Phe Tyr<br>                245                     250                   255 | 768 |
| ccc agc gac atc gcc gtg gag tgg gag agc aat ggg cag ccg gag aac<br>Pro Ser Asp Ile Ala Val Glu Trp Glu Ser Asn Gly Gln Pro Glu Asn<br>             260                     265                   270 | 816 |
| aac tac aag acc acg cct ccc gtg ctg gac tcc gac ggc tcc ttc ttc<br>Asn Tyr Lys Thr Thr Pro Pro Val Leu Asp Ser Asp Gly Ser Phe Phe<br>             275                     280                   285 | 864 |
| ctc tac agc aag ctc acc gtg gac aag agc agg tgg cag cag ggg aac<br>Leu Tyr Ser Lys Leu Thr Val Asp Lys Ser Arg Trp Gln Gln Gly Asn<br>290                      295                     300 | 912 |
| gtc ttc tca tgc tcc gtg atg cat gag gct ctg cac aac cac tac acg<br>Val Phe Ser Cys Ser Val Met His Glu Ala Leu His Asn His Tyr Thr<br>305                      310                     315                   320 | 960 |

```
cag aag agc ctc tcc ctg tct ccg ggt aaa                          990
Gln Lys Ser Leu Ser Leu Ser Pro Gly Lys
                325                 330

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 321
```

```
<212> TYPE: DNA
<213> ORGANISM: Homo sapiens
<220> FEATURE:
<221> NAME/KEY: CDS
<222> LOCATION: (1)..(321)

<400> SEQUENCE: 7 cga act gtg gct gca cca tct gtc ttc atc ttc ccg cca tct gat gag      48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc      96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa     144
Tyr Pro Arg Glu Ala Lys Val Gln Trp Lys Val Asp Asn Ala Leu Gln
        35                  40                  45 tcg ggt aac tca cag gag agc gtc aca gag cag gac agc aag gac agc     192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag     240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg     288
Lys His Lys Val Tyr Ala Cys Glu Val Thr His Gln Gly Leu Ser Ser
                85                  90                  95 ccc gtc aca aag agc ttc aac agg gga gag tgt                         321
Pro Val Thr Lys Ser Phe Asn Arg Gly Glu Cys
            100                 105

<210> SEQ ID NO 8
<211> LENGTH: 107
<212> TYPE: PRT
<213> ORGANISM: Homo sapiens

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTIBODIES AGAINST INSULIN-LIKE GROWTH FACTOR I RECEPTOR AND USES THEREOF

PRIORITY TO RELATED APPLICATIONS

This application is a division of U.S. application Ser. No. 10/886,838, filed Jul. 8, 2004, now pending; which claims the benefit of European Application No. 03015526.1, filed Jul. 10, 2003. The entire contents of the above-identified applications are hereby incorporated as indicated above.

BACKGROUND OF THE INVENTION

Insulin-like growth factor I receptor (IGF-IR, EC 2.7.112, CD 221 antigen) belongs to the family of transmembrane protein tyrosine kinases (LeRoith, D., et al., Endocrin. Rev. 16 (1995) 143-163; and Adams, T. E., et al., Cell. Mol. Life Sci. 57 (2000) 1050-1063). IGF-IR binds IGF-I with high affinity and initiates the physiological response to this ligand in vivo. IGF-IR also binds to IGF-II, however with slightly lower affinity. IGF-IR overexpression promotes the neoplastic transformation of cells and there exists evidence that IGF-IR is involved in malignant transformation of cells and is therefore a useful target for the development of therapeutic agents for the treatment of cancer (Adams, T. E., et al., Cell. Mol. Life Sci. 57 (2000) 1050-1063).

Antibodies against IGF-IR are well-known in the state of the art and investigated for their antitumor effects in vitro and in vivo (Benini, S., et al., Clin. Cancer Res. 7 (2001) 1790-1797; Scotlandi, K., et al., Cancer Gene Ther. 9 (2002) 296-307; Scotlandi, K., et al., Int. J. Cancer 101 (2002) 11-16; Brunetti, A., et al., Biochem. Biophys. Res. Commun. 165 (1989) 212-218; Prigent, S. A., et al., J. Biol. Chem. 265 (1990) 9970-9977; Li, S. L., et al., Cancer Immunol. Immunother. 49 (2000) 243-252; Pessino, A., et al., Biochem. Biophys. Res. Commun. 162 (1989) 1236-1243; Surinya, K. H., et al., J. Biol. Chem. 277 (2002) 16718-16725; Soos, M. A., et al., J. Biol. Chem., 267 (1992) 12955-12963; Soos, M. A., et al., Proc. Natl. Acad. Sci. USA 86 (1989) 5217-5221; O'Brien, R. M., et al., EMBO J. 6 (1987) 4003-4010; Taylor, R., et al., Biochem. J. 242 (1987) 123-129; Soos, M. A., et al., Biochem. J. 235 (1986) 199-208; Li, S. L., et al., Biochem. Biophys. Res. Commun. 196 (1993) 92-98; Delafontaine, P., et al., J. Mol. Cell. Cardiol. 26 (1994) 1659-1673; Kull, F. C. Jr., et al. J. Biol. Chem. 258 (1983) 6561-6566; Morgan, D. O., and Roth, R. A., Biochemistry 25 (1986) 1364-1371; Forsayeth, J. R., et al., Proc. Natl. Acad. Sci. USA 84 (1987) 3448-3451; Schaefer, E. M., et al., J. Biol. Chem. 265 (1990) 13248-13253; Gustafson, T. A., and Rutter, W. J., J. Biol. Chem. 265 (1990) 18663-18667; Hoyne, P. A., et al., FEBS Lett. 469 (2000) 57-60; Tulloch, P. A., et al., J. Struct. Biol. 125 (1999) 11-18; Rohlik, Q. T., et al., Biochem. Biophys. Res. Comm. 149 (1987) 276-281; and Kalebic, T., et al., Cancer Res. 54 (1994) 5531-5534; Adams, T. E., et al., Cell. Mol. Life Sci. 57 (2000) 1050-1063; Dricu, A., et al., Glycobiology 9 (1999) 571-579; Kanter-Lewensohn, L., et al., Melanoma Res. 8 (1998) 389-397; Li, S. L., et al., Cancer Immunol. Immunother. 49 (2000) 243-252). Antibodies against IGF-IR are also described in other publications, e.g., Arteaga, C. L., et al., Breast Cancer Res. Treatment 22 (1992) 101-106; and Hailey, J., et al., Mol. Cancer. Ther. 1 (2002) 1349-1353.

In particular, the monoclonal antibody against IGF-IR called αIR3 is widely used in the investigation of studying IGF-IR mediated processes and IGF-I mediated diseases such as cancer. Alpha-IR-3 was described by Kull, F. C., J. Biol. Chem. 258 (1983) 6561-6566. In addition, about a hundred publications have been published dealing with the investigation and therapeutic uses of αIR3 in regard to its antitumor effect, alone and together with cytostatic agents such as doxorubicin and vincristine. αIR3 is a murine monoclonal antibody which is known to inhibit IGF-I binding to IGF receptor but not IGF-II binding to IGF-IR. αIR3 stimulated at high concentrations tumor cell proliferation and IGF-IR phosphorylation (Bergmann, U., et al., Cancer Res. 55 (1995) 2007-2011; Kato, H., et al., J. Biol. Chem. 268 (1993) 2655-2661). There exist other antibodies (e.g., 1H7, Li, S. L., et al., Cancer Immunol. Immunother. 49 (2000) 243-252) which inhibit IGF-II binding to IGF-IR more potently than IGF-I binding. A summary of the state of the art of antibodies and their properties and characteristics is described by Adams, T. E., et al., Cell. Mol. Life Sci. 57 (2000) 1050-1063.

Most of the antibodies described in the state of the art are of mouse origin. Such antibodies are, however, not useful for the therapy of human patients without further alterations like chimerization or humanization. Based on these drawbacks, human antibodies are clearly preferred as therapeutic agents in the treatment of human patients. Examples of human antibodies against IGF-IR are described in WO 02/053596. However, these antibodies have not been shown to benefit patients in need of antitumor therapy.

There is still a need for human antibodies against IGF-IR having convincing benefits for patients in need of antitumor therapy. The relevant benefit for the patient is, in simple terms, reduction in tumor growth and a significant prolongation of time to progression caused by the treatment with the antitumorigenic agent.

SUMMARY OF THE INVENTION

The present invention relates to antibodies against insulin-like growth factor I receptor (IGF-IR), methods for their production, pharmaceutical compositions containing said antibodies, and uses thereof The invention specifically relates to antibodies which, by inhibiting binding of IGF-1 and IGF-II to IGF-IR, benefit patients in need of antitumor therapy by reducing tumor growth and/or prolonging the time of tumor progression.

BRIEF DESCRIPTION OF THE FIGURES

FIG. 12 Downregulation of IGF-IR exposed on H322N cell surface by antibody 18 in vitro.

DETAILED DESCRIPTION OF THE INVENTION

Figure 1:
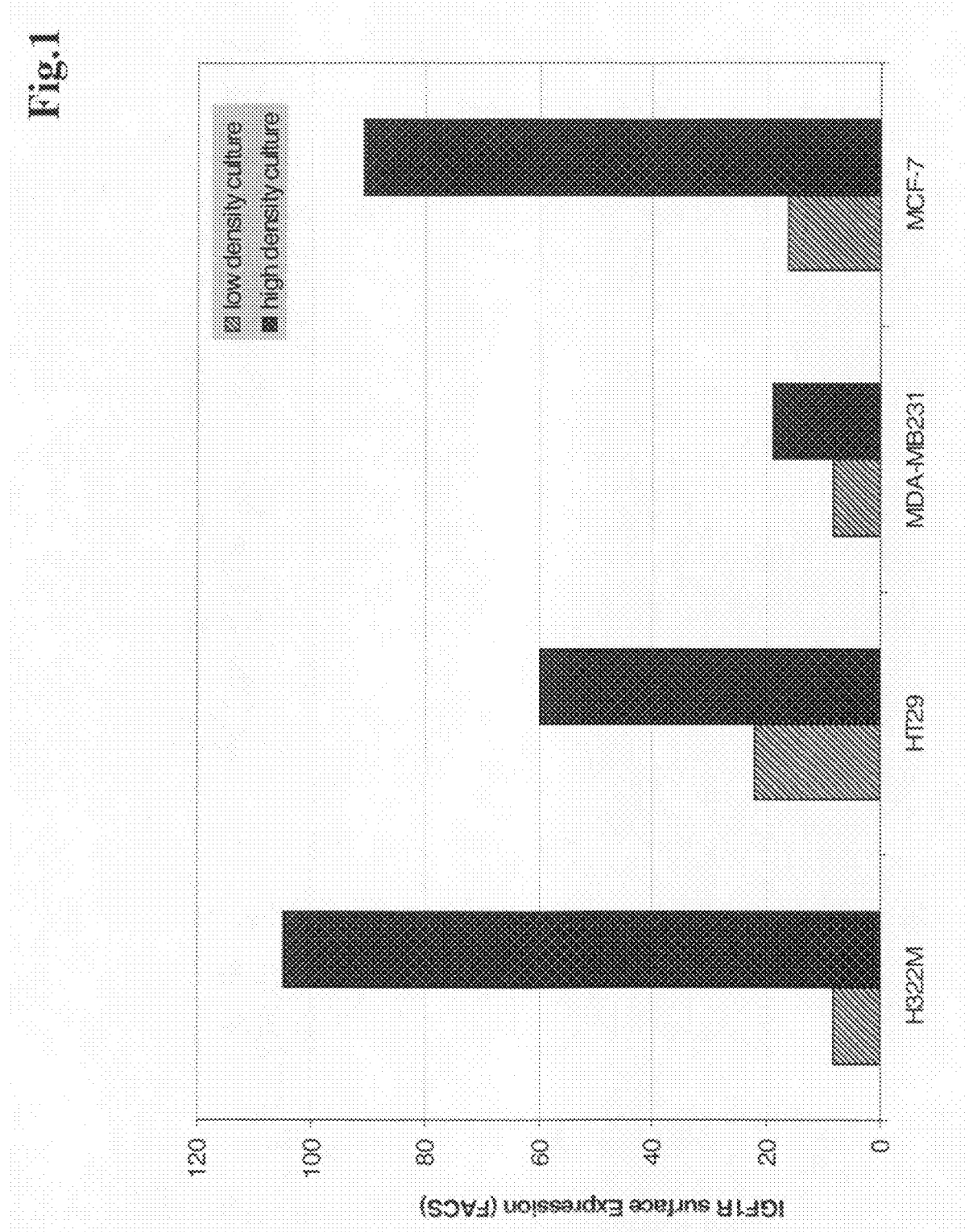
FIG. 1 IGF-IR surface expression in low and high density cell culture.

The invention comprises an antibody binding to IGF-IR which inhibits the binding of IGF-I and IGF-II to IGF-IR, characterized in that said antibody is of IgG1 isotype, and said antibody shows a ratio of $IC_{50}$ values of inhibition of the binding of IGF-I to IGF-IR to the inhibition of binding of IGF-II to IGF-IR of 1:3 to 3:1, and said antibody inhibits IGF-IR phosphorylation at least 80% at a concentration of 5 nM in a cellular phosphorylation assay using HT29 cells in a medium containing 0.5% heat inactivated fetal calf serum (FCS) when compared to such an assay without said antibody; and said antibody shows no IGF-IR stimulating activity measured as IGF-IR phosphorylation at a concentration of 10 μM in a cellular phosphorylation assay using 3T3 cells providing 400,000 to 600,000 molecules IGF-IR per cell in a medium containing 0.5% heat inactivated fetal calf serum (FCS) when compared to such an assay without said antibody.

Antibodies according to the invention show benefits for patients in need of antitumor therapy and provide reduction of tumor growth and a significant prolongation of the time to progression. The antibodies according to the invention have new and inventive properties causing a benefit for a patient suffering from a disease associated with IGF deregulation, especially a tumor disease. The antibodies according to the invention are characterized by the above mentioned properties. The properties are therefore specific binding to IGF-IR, inhibitors of the binding of IGF-I and IGF-II to IGF-IR at the abovementioned ratio, being of IgG1 isotype, and not activating the IGF-IR signaling even in IGF-IR overexpressing cells at a 200-fold concentration of its $IC_{50}$ value. Antibodies having no "IGF-I mimetic activity" provide a strong advantage when used as a therapeutic agent.

Preferably, an antibody according to the invention induces cell death of 20% or more cells of a preparation of IGF-IR expressing cells after 24 hours at a concentration of said antibody of 100 nM by ADCC.

Preferably, the antibodies according to the invention induce cell death of 20% or more cells of a preparation of IGF-IR expressing cells after 4 h at an antibody concentration of 100 nM by CDC.

Preferably, at a concentration of 5 nM the antibodies according to the invention completely inhibit IGF-I mediated signal transduction of IGF-IR in tumor cells.

The invention also comprises nucleic acids. The encoded polypeptides comprise: an antibody heavy chain comprising as CDRs CDR1 (aa 31-35), CDR2 (aa 50-66) and CDR3 (aa 99-107) of SEQ ID NO: 1 or 3; and an antibody light chain comprising as CDRs CDR1 (aa 24-34), CDR2 (aa 50-56) and CDR3 (aa 89-98) of SEQ ID NO:2 or 4.

The antibody is preferably a monoclonal antibody and, in addition, a chimeric antibody (human constant chain), a humanized antibody and especially preferably a human antibody.

The antibody binds to IGF-IR human (EC 2.7.1.112, SwissProt P08069) in competition to antibody 18 (described herein).

The antibody is further characterized by binding to IGF-IR with an affinity of $10^{-8}$ M ($K_D$) or less, preferably of about $10^{-9}$ to $10^{-13}$ M.

The antibody preferably shows no detectable concentration dependent inhibition of insulin binding to the insulin receptor.

Preferably, the invention provides antibodies comprising as complementarity determining regions (CDRs) having the following sequences:

an antibody heavy chain comprising as CDRs CDR1 (aa 31-35), CDR2 (aa 50-66) and CDR3 (aa 99-107) of SEQ ID NO:1 or 3; and an antibody light chain comprising as CDRs CDR1 (aa 24-34), CDR2 (aa 50-56) and CDR3 (aa 89-98) of SEQ ID NO:2 or 4.

The antibody is preferably of the IgG1 type and therefore provides C1q complement binding and induces CDC. The antibody is further characterized by the ability to bind IgGFc receptor and to induce antibody dependent cellular toxicity (ADCC).

The antibody according to the invention considerably prolongates the time to progression in relevant xenograft tumor models in comparison with vehicle treated animals and reduces tumor growth. The antibody inhibits the binding of IGF-I and IGF-II to IGF-IR in vitro and in vivo, preferably in about an equal manner for IGF-I and IGF-II.

The invention further provides hybridoma cell lines which produce such antagonistic monoclonal antibodies according to the invention.

The preferred hybridoma cell lines according to the invention, <IGF-1R> HUMAB Clone 18 (antibody 18) and <IGF-1R> HUMAB Clone 22 (antibody 22), were deposited with Deutsche Sammlung von Mikroorganismen und Zellkulturen GmbH (DSMZ), Mascheroder Weg 1b, D-38124, Germany.

| Cell line | Deposition No. | Date of deposit |
| --- | --- | --- |
| <IGF-1R> HUMAB-Clone 18 | DSM ACC 2587 | Oct. 04, 2003 |
| <IGF-1R> HUMAB-Clone 22 | DSM ACC 2594 | Sep. 05, 2003 |

The antibodies obtainable from said cell lines are preferred embodiments of the invention.

The invention further provides nucleic acids encoding such antibodies, expression vectors containing said nucleic acids, and host cells for the recombinant production of such antibodies.

The invention further provides methods for the recombinant production of such antibodies.

The invention further provides methods for treating cancer, comprising administering to a patient diagnosed as having cancer (and therefore being in need of an antitumor therapy) an effective amount of an antagonistic antibody against IGF-IR according to the invention. The antibody may be administered alone, in a pharmaceutical composition, or alternatively in combination with a cytotoxic treatment such as radiotherapy or a cytotoxic agent or a prodrug thereof.

The invention further comprises the use of an antibody according to the invention for cancer treatment and for the manufacture of a pharmaceutical composition according to the invention. In addition, the invention comprises a method for the manufacture of a pharmaceutical composition according to the invention.

The invention further comprises a pharmaceutical composition containing an antibody according to the invention with a pharmaceutically effective amount, optionally together with a buffer and/or an adjuvant useful for the formulation of antibodies for pharmaceutical purposes.

The invention further provides pharmaceutical compositions comprising such antibodies in a pharmaceutically acceptable carrier. In one embodiment, the pharmaceutical composition may be included in an article of manufacture or kit.

The invention further comprises a vector containing a nucleic acid according to the invention, capable of expressing said nucleic acid in a prokaryotic or eukaryotic host cell.

The invention further comprises a prokaryotic or eukaryotic host cell comprising a vector according to the invention.

The invention further comprises a method for the production of a recombinant human antibody according to the invention, characterized by expressing a nucleic acid according to the invention in a prokaryotic or eukaryotic host cell and recovering said antibody from said cell. The invention further comprises the antibody obtainable by such a recombinant method.

The invention further comprises a method for the selection of an antibody against IGF-IR from a plurality of antibodies against IGF-IR characterized in that a cellular phosphorylation assay using 3T3 cells providing 400,000 to 600,000 molecules IGF-IR per cell in a medium containing 0.5% heat inactivated fetal calf serum (FCS) is performed with said antibodies and said antibody is selected which shows no IGF-IR stimulating activity measured as PKB phosphorylation at a concentration of 10 µM when compared to such an assay without said antibody. Preferably the antibody has one or more of the above mentioned additional properties.

The invention further comprises a method for the preparation of a pharmaceutical composition characterized in selecting an antibody against IGF-IR from a plurality of antibodies against IGF-IR, performing a cellular phosphorylation assay using 3T3 cells providing 400,000 to 600,000 molecules IGF-IR per cell in a medium containing 0.5% heat inactivated fetal calf serum (FCS) with said antibodies and selecting said antibody which shows no IGF-IR stimulating activity measured as PKB phosphorylation at a concentration of 10 µM when compared to such an assay without said antibody, producing said antibody by means of recombinant expression, recovering said antibody and combining said antibody with a pharmaceutical acceptable buffer and/or adjuvant. Preferably the antibody has one or more of the above mentioned additional properties.

The term "antibody" encompasses the various forms of antibodies including but not being limited to whole antibodies, antibody fragments, human antibodies, humanized antibodies and genetically engineered antibodies as long as the characteristic properties according to the invention are retained.

"Antibody fragments" comprise a portion of a full length antibody, generally at least the antigen binding portion or the variable region thereof. Examples of antibody fragments include diabodies, single-chain antibody molecules, immunotoxins, and multispecific antibodies formed from antibody fragments. In addition, antibody fragments comprise single chain polypeptides having the characteristics of a VH chain, namely being able to assemble together with a VL chain or of a VL chain binding to IGF-1R, namely being able to assemble together with a VH chain to a functional antigen binding pocket and thereby providing the property of inhibiting the binding of IGF-I and IGF-II to IGF-IR.

"Antibody fragments" also comprises such fragments which per se are not able to provide effector functions (ADCC/CDC) but provide this function in a manner according to the invention after being combined with appropriate antibody constant domain(s).

The terms "monoclonal antibody" or "monoclonal antibody composition" as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g. a transgenic mouse, having a genome comprising a human heavy chain transgene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric and bifunctional antibodies.

The term "human antibody", as used herein, is intended to include antibodies having variable and constant regions derived from human germline immunoglobulin sequences. The variable heavy chain is preferably derived from germline sequence DP-50 (GenBank LO6618) and the variable light chain is preferably derived from germline sequence L6 (GenBank X01668). The constant regions of the antibody are constant regions of human IgG1 type. Such regions can be allotypic and are described by, e.g., Johnson, G., and Wu, T. T., Nucleic Acids Res. 28 (2000) 214-218 and the databases referenced therein and are useful as long as the properties of induction of ADCC and preferably CDC according to the invention are retained.

The term "recombinant human antibody", as used herein, is intended to include all human antibodies that are prepared, expressed, created or isolated by recombinant means, such as antibodies isolated from a host cell such as an SP2-0, NS0 or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the VH and VL regions of the recombinant antibodies are sequences that, while derived from and related to human germline VH and VL sequences, may not naturally exist within the human antibody germline repertoire in vivo.

As used herein, "binding" refers to antibody binding to IGF-IR with an affinity of about $10^{-13}$ to $10^{-8}$ M ($K_D$), preferably of about $10^{-13}$ to $10^{-9}$ M.

The term "nucleic acid molecule", as used herein, is intended to include DNA molecules and RNA molecules. A nucleic acid molecule may be single-stranded or double-stranded, but preferably is double-stranded DNA.

The "constant domains" are not involved directly in binding the antibody to an antigen but are involved in the effector functions (ADCC, complement binding, and CDC). The constant domain of an antibody according to the invention is of the IgG1 type. Human constant domains having these characteristics are described in detail by Kabat et al., Sequences of Proteins of Immunological Interest, 5th Ed. Public Health Service, National Institutes of Health, Bethesda, Md. (1991), and by Brüggemann, M., et al., J. Exp. Med. 166 (1987) 1351-1361; Love, T. W., et al., Methods Enzymol. 178 (1989) 515-527. Examples are shown in SEQ ID NOS:5 to 8. Other useful and preferred constant domains are the constant domains of the antibodies obtainable from the hybridoma cell lines deposited with DSMZ for this invention. The constant domains useful in the invention provide complement binding. ADCC and optionally CDC are provided by the combination of variable and constant domains.

The "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat et al., Sequences of Proteins of Immunological Interest, 5th Ed. Public Health Service, National Institutes of Health, Bethesda, Md. (1991)) and/or those residues from a "hypervariable loop".

The term "binding to IGF-IR" as used herein means the binding of the antibody to IGF-IR in an in vitro assay, preferably in a binding assay in which the antibody is bound to a surface and binding of IGF-IR is measured by Surface Plasmon Resonance (SPR). Binding means a binding affinity ($K_D$) of $10^{-8}$ M or less, preferably $10^{-13}$ to $10^{-9}$ M.

Binding to IGF-IR can be investigated by a BIAcore assay (Pharmacia Biosensor AB, Uppsala, Sweden). The affinity of the binding is defined by the terms ka (rate constant for the association of the antibody from the antibody/antigen complex), kd (dissociation constant), and $K_D$ (kd/ka). The antibodies according to the invention show a $K_D$ of $10^{-10}$ M or less.

The binding of IGF-I and IGF-II to IGF-IR is inhibited by the antibodies according to the invention. The inhibition is measured as $IC_{50}$ in an assay for binding of IGF-I/IGF-II to IGF-IR on tumor cells. Such an assay is described in Example 7. In such an assay, the amount of radiolabeled IGF-I or IGF-II or IGF-IR binding fragments thereof bound to the IGF-IR provided at the surface of said tumor cells (e.g. HT29) is measured without and with increasing concentrations of the antibody. The $IC_{50}$ values of the antibodies according to the invention for the binding of IGF-I and IGF-II to IGF-IR are no more than 2 nM and the ratio of the $IC_{50}$ values for binding of IGF-I/IGF-II to IGF-IR is about 1:3 to 3:1. $IC_{50}$ values are measured as average or median values of at least three independent measurements. Single $IC_{50}$ values may be out of the scope.

The term "inhibiting the binding of IGF-I and IGF-II to IGF-IR" as used herein refers to inhibiting the binding of $I^{125}$-labeled IGF-I or IGF-II to IGF-IR presented on the surface of HT29 (ATCC HTB-38) tumor cells in an in vitro assay. Inhibiting means an $IC_{50}$ value of 2 nM or lower.

The term "IGF-IR expressing cells" refers to such cells which are overexpressing IGF-I receptor to about at least 20,000 receptors/cell. Such cells are, for example, tumor cell lines such as NCI H322M or HT29, or a cell line (e.g. 3T3 ATCC CRL1658) overexpressing IGF-IR after transfection with an expression vector for IGF-IR. The amount of receptors per cell is measured according to Lammers et al EMBO J, 8 (1989) 1369-1375.

The term "inhibiting of IGF-IR phosphorylation" refers to a cellular phosphorylation assay using 3T3 cells providing 400,000 to 600,000 molecules IGF-IR per cell in a medium containing 0.5% heat inactivated fetal calf serum (FCS) when compared to such an assay without said antibody. Phosphorylation is detected by Western blotting using an antibody specific for tyrosine-phosphorylated proteins. Such an assay is described in Example 11. Heat inactivation of FCS is performed by short term heating to 56° C. for inactivation of the complement system.

The term "inhibiting of PKB phosphorylation" refers to a cellular phosphorylation assay using 3T3 cells providing 400,000 to 600,000 molecules IGF-IR per cell in a medium containing 0.5% heat inactivated fetal calf serum (FCS) when compared to such an assay without said antibody. Phosphorylation is detected by Western blotting using an antibody specific for PKB phosphorylated at serine 473 of PKB (Akt 1, Swiss Prot Acc. No. P31749). Such an assay is described in Example 11.

The term "antibody-dependent cellular cytotoxicity (ADCC)" refers to lysis of human tumor target cells by an antibody according to the invention in the presence of effector cells. ADCC is measured preferably by the treatment of a preparation of IGF-IR expressing cells with an antibody according to the invention in the presence of effector cells such as freshly isolated PBMC or purified effector cells from buffy coats, like monocytes or NK cells. ADCC is found if the antibody induces at a concentration of 100 nM the lysis (cell death) of 20% or more of the tumor cells after 24 hours. If ADCC is found to be more pronounced at 4 h than at 24 h, then measurement is performed at 4 h. The assay is performed preferably with $^{51}$Cr or Eu labeled tumor cells and measurement of specifically released $^{51}$Cr or Eu. Controls include the incubation of the tumor target cells with effector cells but without the antibody.

The term "complement-dependent cytotoxicity (CDC)" refers to lysis of human tumor target cells by the antibody according to the invention in the presence of complement. CDC is measured preferably by the treatment of a preparation of IGF-IR expressing cells with an antibody according to the invention in the presence of complement. CDC is found if the antibody induces at a concentration of 100 nM the lysis (cell death) of 20% or more of the tumor cells after 4 hours. The assay is performed preferably with $^{51}$Cr or Eu labeled tumor cells and measurement of released $^{51}$Cr or Eu. Controls include the incubation of the tumor target cells with complement but without the antibody.

The term "complete inhibition of IGF-I mediated signal transduction" refers to the inhibition of IGF-1-mediated phosphorylation of IGF-IR. For such an assay, IGF-IR expressing cells, preferably H322M cells, are stimulated with IGF-I and treated with an antibody according to the invention (an antibody concentration of 5 nM or higher is useful). Subsequently, an SDS PAGE is performed and phosphorylation of IGF-IR is measured by Western blotting analysis with an antibody specific for phosphorylated tyrosine. Complete inhibition of the signal transduction is found if on the Western blot visibly no band can be detected which refers to phosphorylated IGF-IR.

The antibodies according to the invention show a binding to the same epitope of IGF-IR as antibody 18 or are inhibited in binding to IGF-IR due to steric hindrance of binding by antibody 18. Binding inhibition can be detected by an SPR assay using immobilized antibody 18 and IGF-IR at a concentration of 20-50 nM and the antibody to be detected at a concentration of 100 nM. A signal reduction of 50% or more shows that the antibody competes with antibody 18. Such an assay can be performed in the same manner by using antibody 22 as an immobilized antibody.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The antibodies according to the invention include, in addition, such antibodies having "conservative sequence modifications", nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-IGF-IR antibody can be preferably replaced with another amino acid residue from the same side chain family.

Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

In a preferred embodiment of the invention, the antibodies according to the invention are further characterized by one or more of the characteristics selected from the group selected from the binding parameters ka, kd and $K_D$, binding to the same epitope to which antibodies 18 and 22 bind, the $IC_{50}$ values for inhibition of binding of IGF-I and IGF-II to IGF-IR on tumor cells, and the $IC_{50}$ values for inhibition of phosphorylation of IGF-IR upon stimulation of IGF-I in tumor cells. Inhibition of phosphorylation of IGF-IR leads to the inhibition of phosphorylation of downstream elements such as PKB, the down-regulation of IGF-IR in tumor cells, and the influence on the three-dimensional growth of tumor cells in vitro. The antibodies are further preferably characterized by their pharmacokinetic and pharmacodynamic values, and the cross-reactivity for other species.

The antibodies according to the invention inhibit IGF-IR phosphorylation of tyrosine and preferably also PKB phosphorylation of tyrosine to a similar extent.

The antibodies according to the invention preferably downregulate the IGF-IR protein level in tumor cells and in tumors, e.g. xenograft tumors.

The antibodies according to the invention inhibit preferably the three-dimensional growth of tumor cells in a colony formation assay as well as proliferation of IGF-IR expressing cells (e.g. NIH 3T3 cells).

The antibodies according to the invention preferably do not inhibit binding of insulin to insulin receptor in a binding competition assay on insulin receptor overexpressing 3T3 cells using the antibody in a concentration of 200 nmol/l.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/ SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants of human IGF-IR antibody are prepared by introducing appropriate nucleotide changes into the antibody DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability or facilitate the purification.

Any cysteine residue not involved in maintaining the proper conformation of the anti-IGF-IR antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-IGF-IR antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-IGF-IR antibody.

The invention also pertains to immunoconjugates comprising the antibody according to the invention conjugated to a cytotoxic agent such as a chemotherapeutic agent, toxin (e.g., an enzymatically active toxin of bacterial, fungal, plant or animal origin, or fragments thereof), a radioactive isotope (i.e., a radioconjugate) or a prodrug of a cytotoxic agent. Agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters; (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediatnine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta, E. S., et al., Science 238 (1987) 1098-1104). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin, J. D., and Wriston, J. C. Jr., CRC Crit. Rev. Biochem. (1981) 259-306.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr, H. T., and Bahl, O. P., Arch. Biochem. Biophys. 259 (1987) 52-57 and by Edge, A. S., et al. Anal. Biochem. 118 (1981) 131-137. Enzymatic cleavage of carbohydrate moieties on antibodies can be achieved by the use of a variety of endo- and exoglycosidases as described by Thotakura, N. R., and Bahl, O. P., Meth. Enzymol. 138 (1987) 350-359.

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In yet another aspect, the invention provides isolated B-cells from a transgenic non-human animal, e.g. a transgenic mouse, which express the human anti IGF-IR antibodies according to the invention. Preferably, the isolated B cells are obtained from a transgenic non-human animal, e.g., a transgenic mouse, which has been immunized with a purified or enriched preparation of IGF-IR antigen and/or cells expressing IGF-IR. Preferably, the transgenic non-human animal, e.g. a transgenic mouse, has a genome comprising a human heavy chain transgene and a human light chain transgene encoding all or a portion of an antibody of the invention. The isolated B-cells are then immortalized to provide a source (e.g. a hybridoma) of human anti-IGF-IR antibodies. Accordingly, the present invention also provides a hybridoma capable of producing human monoclonal antibodies according to the invention. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell.

In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of IGF-IR antigen and/or cells expressing IGF-IR. Preferably, the transgenic non-human animal, e.g. the transgenic mouse, is capable of producing IgG1 isotypes of human monoclonal antibodies to IGF-IR.

The human monoclonal antibodies according to the invention can be produced by immunizing a transgenic non-human animal, e.g. a transgenic mouse, having a genome comprising a human heavy chain transgene and a human light chain transgene encoding all or a portion of an antibody of the invention, with a purified or enriched preparation of IGF-IR antigen and/or cells expressing IGF-IR. B cells (e.g. splenic B cells) of the animal are then obtained and fused with myeloma cells to form immortal, hybridoma cells that secrete human monoclonal antibodies against IGF-IR.

In a preferred embodiment, human monoclonal antibodies directed against IGF-IR can be generated using transgenic mice carrying parts of the human immune system rather than the mouse system. These transgenic mice, referred to herein as "HuMAb" mice, contain a human immunoglobulin gene minilocus that encodes unrearranged human immunoglobulin genes which include the heavy ($\mu$ and $\gamma$) and $\kappa$ light chain (constant region genes), together with targeted mutations that inactivate the endogenous $\mu$ and $\kappa$ chain loci (Lonberg, N., et al., Nature 368 (1994) 856-859). Accordingly, the mice exhibit reduced expression of mouse IgM or K, and in response to immunization, the introduced human heavy and light chain transgenes undergo class switching and somatic mutation to generate high affinity human IgG monoclonal antibodies (Lonberg, N., et al., Nature 368 (1994) 856-859; reviewed in Lonberg, N., Handbook of Experimental Pharmacology 113 (1994) 49-101; Lonberg, N., and Huszar, D., Intern. Rev. Immunol. 25 (1995) 65-93; and Harding, F., and Lonberg, N., Ann. N. Acad. Sci 764 (1995) 536-546). The preparation of HuMAb mice is described in Taylor, L., et al., Nucleic Acids Research 20 (1992) 6287-6295; Chen, J., et al., International Immunology 5 (1993) 647-656; Tuaillon, N., et al., Proc. Natl. Acad. Sci USA 90 (1993) 3720-3724; Choi, T. K., et al., Nature Genetics 4 (1993) 117-123; Chen, J., et al., EMBO J. 12 (1993) 821-830; Tuaillon, N., et al., Immunol. 152 (1994) 2912-2920; Lonberg, N., et al., Nature 368 (1994) 856-859; Lonberg, N., Handbook of Experimental Pharmacology 113 (1994) 49-101; Taylor, L., et al., Int. Immunol. 6 (1994) 579-591; Lonberg, N., and Huszar, D., Intern. Rev. Immunol. 25 (1995) 65-93; Harding, F., and Lonberg, N., Ann. N. Acad. Sci 764 (1995) 536-546; Fishwild, D. M., et al., Nat. Biotechnol. 14 (1996) 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,545,807; 5,770,429; WO 98/24884; WO 94/25585; WO 93/1227; WO 92/22645; and WO 92/03918.

To generate fully human monoclonal antibodies to IGF-IR, HuMAb mice can be immunized with a purified or enriched preparation of IGF-IR antigen and/or cells expressing IGF-IR in accordance with the general method, as described by Lonberg, N., et al., Nature 368 (1994) 856-859; Fishwild, D. M., et al., Nat. Biotechnol. 14 (1996) 845-851 and WO 98/24884. Preferably, the mice will be 6-16 weeks of age upon the first immunization. For example, a purified or enriched preparation of soluble IGF-IR antigen (e.g. purified from IGF-IR-expressing cells) can be used to immunize the HuMAb mice intraperitoneally. In the event that immunizations using a purified or enriched preparation of IGF-IR antigen do not result in antibodies, mice can also be immunized with cells expressing IGF-IR, e.g., a tumor cell line, to promote immune responses. Cumulative experience with various antigens has shown that the HuMAb transgenic mice respond best when initially immunized intraperitoneally (i.p.) with antigen in complete Freund's adjuvant, followed by every other week i.p. immunizations (for example, up to a total of 6) with antigen in incomplete Freund's adjuvant. The immune response can be monitored over the course of the immunization protocol with plasma samples being obtained by retroorbital bleeds. The plasma can be screened by ELISA, and mice with sufficient titers of anti-IGF-IR human immunoglobulin can be used for immortalization of corresponding B cells. Mice can be boosted intravenously with antigen 3 to 4 days before sacrifice and removal of the spleen and lymph nodes. It is expected that 2-3 fusions for each antigen may need to be performed. Several mice will be immunized for each antigen. For example, a total of twelve HuMAb mice of the HCo7 and HCo12 strains can be immunized.

The HCo7 mice have a JKD disruption in their endogenous light chain (kappa) genes (as described in Chen, J., et al., EMBO J. 12 (1993) 821-830), a CMD disruption in their endogenous heavy chain genes (as described in Example 1 of WO 01/14424), a KCo5 human kappa light chain transgene (as described in Fishwild, D. M., et al., Nat. Biotechnol. 14 (1996) 845-851), and a HCo7 human heavy chain transgene (as described in U.S. Pat. No. 5,770,429).

The HCo12 mice have a JKD disruption in their endogenous light chain (kappa) genes (as described in Chen, J., et al., EMBO J. 12 (1993) 821-830), a CMD disruption in their endogenous heavy chain genes (as described in Example 1 of WO 01/14424), a KCo5 human kappa light chain transgene (as described in Fishwild, D. M., et al., Nat. Biotechnol. 14 (1996) 845-851), and a HCo12 human heavy chain transgene (as described in Example 2 of WO 01/14424).

The mouse lymphocytes can be isolated and fused with a mouse myeloma cell line using PEG based on standard protocols to generate hybridomas. The resulting hybridomas are then screened for the production of antigen-specific antibodies. For example, single cell suspensions of splenic and lymph node-derived lymphocytes from immunized mice are fused to one-sixth the number of SP 2/0 nonsecreting mouse myeloma cells (ATCC, CRL 1581) with 50% PEG. Cells are plated at approximately $2 \times 10^5$ in flat bottom microtiter plate, followed by about two weeks incubation in selective medium.

Individual wells are then screened by ELISA for human anti-IGF-IR monoclonal IgM and IgG antibodies. Once extensive hybridoma growth occurs, medium is analyzed, usually after 10-14 days. The antibody secreting hybridomas are replated, screened again, and if still positive for human IgG, anti-IGF-IR monoclonal antibodies, can be subcloned at least twice by limiting dilution. The stable subclones are then cultured in vitro to produce antibody in tissue culture medium for characterization.

Because CDR sequences are responsible for antibody-antigen interactions, it is possible to express recombinant antibodies according to the invention by constructing expression vectors that include the CDR sequences according to the invention onto framework sequences from a different human antibody (see, e.g., Riechmann, L., et al., Nature 332 (1998) 323-327; Jones, P., et al., Nature 321 (1986) 522-525; and Queen, C., et al., Proc. Natl. Acad. See. U.S.A. 86 (1989) 10029-10033). Such framework sequences can be obtained from public DNA databases that include germline human antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region.

The invention preferably comprises a nucleic acid fragment encoding a polypeptide binding to IGF-IR, whereby said polypeptide inhibits the binding of IGF-I and IGF-II to IGF-IR, selected from the group consisting of said polypeptide comprising an antibody heavy chain comprising as CDRs CDR1 (aa 31-35), CDR2 (aa 50-66) and CDR3 (aa 99-107) of SEQ ID NO:1 or 3; and an antibody light chain comprising as CDRs CDR1 (aa 24-34), CDR2 (aa 50-56) and CDR3 (aa 89-98) of SEQ ID NO:2 or 4.

The reconstructed heavy and light chain variable regions are combined with sequences of promoter, translation initiation, constant region, 3' untranslated, polyadenylation, and transcription termination to form expression vector constructs. The heavy and light chain expression constructs can be combined into a single vector, co-transfected, serially transfected, or separately transfected into host cells which are then fused to form a single host cell expressing both chains.

Accordingly, the invention provides a method for the production of a recombinant human antibody according to the invention, characterized by expressing a nucleic acid encoding an antibody heavy chain comprising as CDRs CDR1 (aa 31-35), CDR2 (aa 50-66) and CDR3 (aa 99-107) of SEQ ID NO:1 or 3; and an antibody light chain comprising as CDRs CDR1 (aa 24-34), CDR2 (aa 50-56) and CDR3 (aa 89-98) of SEQ ID NO:2 or 4.

The invention further comprises the use of an antibody according to the invention for the diagnosis of IGF-IR in vitro, preferably by an immunological assay determining the binding between IGF-IR of a sample and the antibody according to the invention.

In another aspect, the present invention provides a composition, e.g. a pharmaceutical composition, containing one or a combination of human monoclonal antibodies, or the antigen-binding portion thereof, of the present invention, formulated together with a pharmaceutically acceptable carrier.

Pharmaceutical compositions of the invention also can be administered in combination therapy, i.e., combined with other agents. For example, the combination therapy can include a composition of the present invention with at least one anti-tumor agent or other conventional therapy.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Taxotere (docetaxel), Busulfan, Gemcitabine, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see U.S. Pat. No. 4,675,187), Melphalan and other related nitrogen mustards.

The term "cytotoxic agent" as used herein refers to a substance that inhibits or prevents the function of cells and/or causes destruction of cells. The term is intended to include radioactive isotopes, chemotherapeutic agents, and toxins such as enzymatically active toxins of bacterial fungal, plant or animal origin, or fragments thereof.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986), and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam ring prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A "pharmaceutically acceptable salt" refers to a salt that retains the desired biological activity of the antibody and does not impart any undesired toxicological effects (see e.g. Berge, S. M., et al., J. Pharm. Sci. 66 (1977) 1-19). Such salts are included in the invention. Examples of such salts include acid addition salts and base addition salts. Acid addition salts include those derived from nontoxic inorganic acids, such as hydrochloric salts.

A composition of the present invention can be administered by a variety of methods known in the art. As will be appreciated by the skilled artisan, the route and/or mode of administration will vary depending upon the desired results.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The following examples, references, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO: 1-4 Nucleotide and amino sequences of light and heavy variable region domains of antibodies 18 and 22

SEQ ID NO: 5 and 6 Nucleotide and amino sequences of human constant region domain

EXAMPLE 1

Generation of a Hybridoma Cell Line Producing Anti-IGF-IR Antibodies

Culture of Hybridomas

Generated HuMAb hybridomas were cultured in Hybridoma Express Medium (PAA Laboratories GmbH, Austria) supplemented with 2 mM L-glutamine (BioWhittaker) and 4% Origen Cloning Factor (Igen, France) at 37° C. and 5% $CO_2$.

Immunization Procedure of Transgenic Mice

Ten HCo7 transgenic mice (4 males and 6 females), strain GG2201 (Medarex, San José, Calif., USA) were alternatingly immunized with $1\times10^6$ NIH 3T3 cells, transfected with an expression vector for IGF-IR, and 20 µg soluble extracellular domain of IGF-IR. Six immunizations were performed in total, three intraperitoneal (IP) immunizations with the IGF-IR expressing cells and three subcutaneous (SC) immunizations at the tail base with the recombinant protein. For the first immunization, 100 µl of $1\times10^6$ NIH 3T3 IGF-IR cells was mixed with 100 µl complete Freunds' adjuvant (CFA; Difco Laboratories, Detroit, USA). For all other immunizations, 100 µl of cells in PBS were used or recombinant protein was mixed with 100 µl incomplete Freunds' adjuvant (ICFA; Difco).

Antigen Specific ELISA

Anti-IGF-IR titers in sera of immunized mice were determined by antigen specific ELISA. IGF-IR soluble extracellular domain at a concentration of 1 µg/ml in PBS was coated overnight at 4° C., or for two hours at 37° C., to 96 wells plates. Thereafter, the wells were blocked with PBSTC (PBS supplemented with 0.05% Tween®-20 and 2% chicken serum (Gibco BRL)) for 1 hour (h) at room temperature. First tap sera were diluted 1/50 in PBSTC, sera from all other taps were pre-diluted 1/100 in PBSTC and serially diluted up to 1/6400. Diluted sera were added to the wells and incubated for 1 h at 37° C. Pre-tap serum was used as negative control. 200 ng/ml goat anti-human IGF-IR (100 µg/ml) was used as positive control. Subsequently, plates were washed twice with PBST and incubated with horse radish peroxidase (HRP)-conjugated rat anti-human IgG F(ab')$_2$ (DAKO), diluted 1/2000 in PBSTC for 1 h at 37° C. Wells were washed twice with PBST and assays were developed with freshly prepared ABTS®0 solution (1 mg/ml) (ABTS: 2,2'-azino bis(3-ethylbenzthiazoline-6-sulfonic acid) for 30 minutes at room temperature (RT) in the dark. Absorbance was measured at 405 nm.

FACS Analysis

In addition to determination by antigen specific ELISA, anti-IGF-IR titers in sera of immunized mice were also determined by FACS analyses. NIH 3T3 IGF-IR cells and the non-transfected NIH 3T3 IGF-IR cells were incubated with diluted sera for 30 minutes at 4° C. Pre-tap serum was used as negative control. Initially, 200 ng/ml goat anti-human IGF-IR was used as positive control. Cells were washed three times in PBS supplemented with 1% bovine serum albumin and 0.01% azide. Subsequently, cells were incubated with fluorescein isothiocyanate (FITC)-conjugated antigen binding fragments (F(ab')$_2$ fragments) of rat anti-human human IgG diluted 1/100 in FACS buffer, for 30 minutes at 4° C. Cells were washed twice in FACS buffer and samples were analyzed on a FACSCalibur (Becton Dickinson, Erembodegem-Aalst, Belgium).

Boosting of Mice

When serum titers of anti-IGF-IR were found to be sufficient, mice were additionally boosted twice with 15 µg IGF-IR extracellular domain in 200 µl PBS intravenously (i.v.) 4 and 3 days before fusion.

Hybridoma Generation

Mice were sacrificed and the spleen and lymph nodes flanking the abdominal aorta and vena cava were collected. Fusion of splenocytes and lymph node cells with the fusion partner SP 2.0 cells was performed according to standard operating procedures.

κ-ELISA

To determine whether hybridomas that resulted from the fusion generate human antibodies, a κ-ELISA was performed. ELISA plates were coated with rat anti-human IgG κ-light chain antibody (DAKO) diluted 1/10000 in PBS by overnight incubation at 4° C. After discarding the wells, plates were blocked by incubation with PBSTC for 1 hour at room temperature. Thereafter, wells were incubated with hybridoma culture supernatant, 1/2 diluted in PBSTC. Culture medium 1/2 diluted in PBSTC was used as negative control, κ-light positive mouse serum 1/100 diluted in PBSTC served as positive control. Subsequently, wells were washed thrice and were incubated with HRP-conjugated rat anti-human IgG F(ab')$_2$ (DAKO), diluted 1/2000 in PBSTC for 1 h at 37° C. Wells were washed thrice and assays were developed with freshly prepared ABTS® solution (1 mg/ml) for 30 minutes at room temperature (RT) in the dark. Absorbance was measured at 405 nm in an ELISA plate reader.

The monoclonal antibodies 18 and 22 were prepared.

EXAMPLE 2

Determination of the Affinity of Anti-IGF-IR Antibodies to IGF-IR

| Instrument: | BIACORE ® 3000 |
|---|---|
| Chip: | CM5 |
| Coupling: | amine coupling |
| Buffer: | HBS (HEPES, NaCl), pH 7.4, 25° C. |

For affinity measurements anti human FCγ antibodies (from rabbit) have been coupled to the chip surface for presentation of the antibody against IGF-IR. IGF-IR extracellular domain was added in various concentrations in solution. Association was measured by an IGF-1R-injection of 3 minutes; dissociation was measured by washing the chip surface with buffer for 5 minutes. The affinity data for antibodies 18 and 22 are shown in Table 1.

TABLE 1

Affinity data measured by SPR (BIACORE ® 3000)

| Antibody | ka (1/Ms) | kd (1/s) | KD (M) |
|---|---|---|---|
| 18 | $1.49 \times 10^5$ | $1.03 \times 10^{-7}$ | $6.95 \times 10^{-13}$ |
| 22 | $1.47 \times 105$ | $9.64 \times 10^{-5}$ | $6.56 \times 10^{-10}$ |

EXAMPLE 3

Three-dimensional Growth of Tumor Cells and Overexpression of IGF-I Receptor at Cell-cell-contact (3D Culture)

Materials and Methods:

NCI H322M cells were cultured in RPMI media on optical grade glass cover slides either at low density or superconfluent to study the effects on IGF-IR surface expression. In parallel, H322M xenograft tissue isolated from the control group (untreated mice) was shock frozen in isopentane and kryosections were cut at 5 µm thickness. Immunofluorescence labelling was performed using a mouse-anti IGF-IR monoclonal antibody (αIR3, 5 µg/ml) or an antibody according to the invention, followed by a goat anti-mouse-antibody or a goat anti-mouse antibody labeled with Cy3 (Amersham Biosciences, GB) or Alexa Fluor® 488 (Molecular Probes, Inc., USA). Specimens were imaged on a Leica SP2 confocal microscope or analyzed by FACS.

Results:

When H322M cells cultured at high density were imaged by confocal microscopy it became apparent that IGF-IR clustered specifically at the sites of cell-cell contact. When compared to H322M cells grown in vivo, i.e. xenograft tissue, there was a striking similarity to densely packed in vitro cultures as far as the organization of surface IGF-I receptors was concerned.

The upregulation of surface IGF-I receptor in superconfluent cultures of H322M cells was also quantified by FACS. IGF-I receptor surface expression increased more than 10 fold when cells were grown under high density conditions compared to low density without significant cell-cell contacts.

Other tumor cells such as HT29, MDA231 and MCF-7 showed a similar behavior, indicating that upregulation of IGF-I receptors on the cell surface upon establishing cell-cell contact sites is not an unique feature of H322M cells but appears to be a general property of a more tissue like organization that is also found in vivo (FIG. 1).

EXAMPLE 4

Growth Inhibition of H322M Tumor Cells Expressing IGF-IR in 3D Culture Under Treatment with Antibody 18 (WST-Assay)

Figure 2:
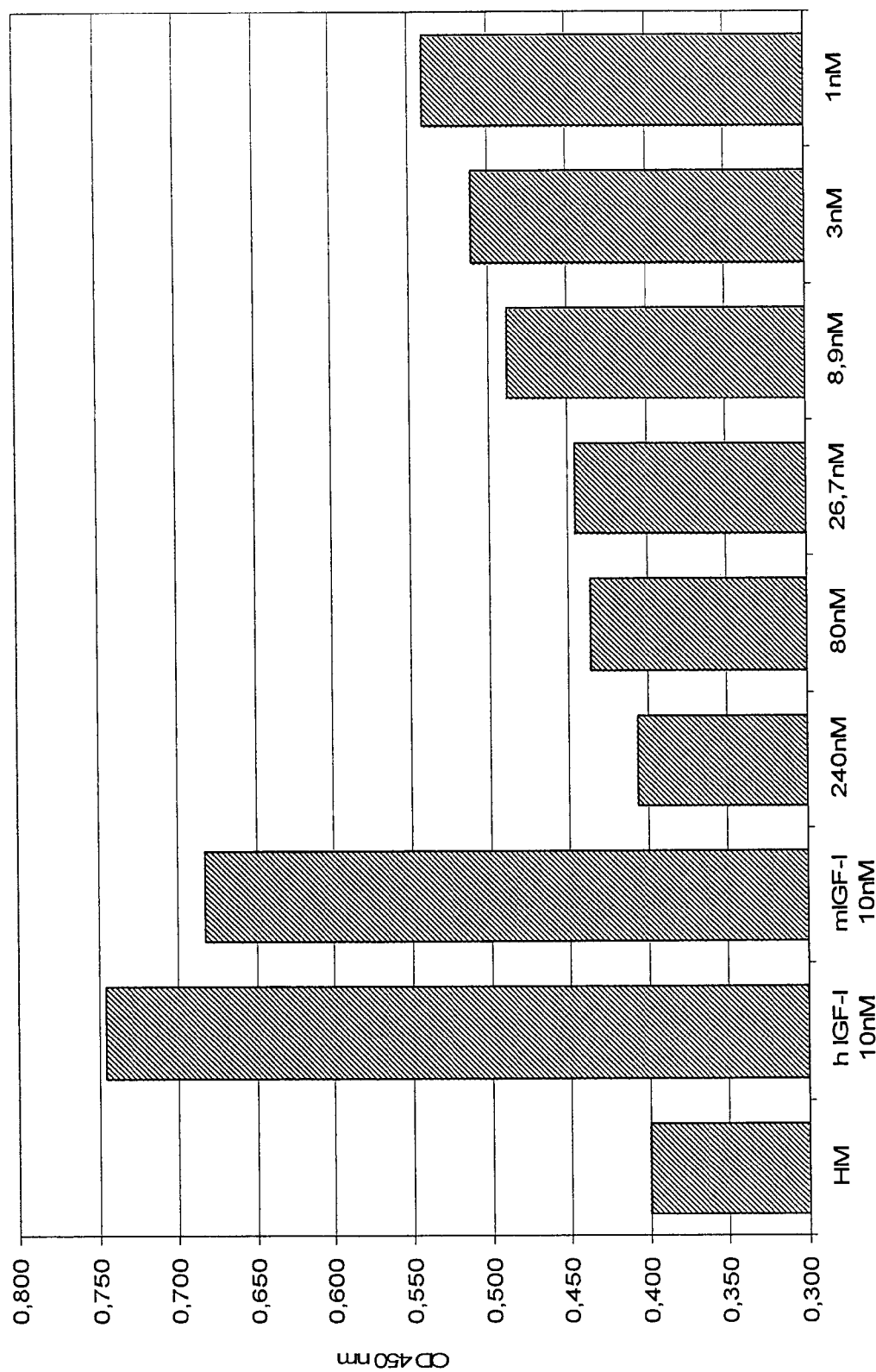
FIG. 2 WST assay (NCI H322M cells) for proliferation inhibition in 3D culture.

H322M cells were cultured in RPMI1640/0.5% FCS media on poly-HEMA (poly(2-hydroxyethylmethacrylate)) coated dishes to prevent adherence to the plastic surface. Under these conditions H322M cells form dense spheroids that grow three dimensionally (a property that is called anchorage independence). These spheroids resemble closely the three dimensional histoarchitecture and organization of solid tumors in situ. Spheroid cultures were incubated for 5 days in the presence of increasing amounts of antibodies from 0-240 nM. The WST conversion assay was used to measure growth inhibition. When H322M spheroid cultures were treated with different concentrations of antibody 18 (1-240 nM) a dose dependent inhibition in growth could be observed (FIG. 2).

EXAMPLE 5

Growth Inhibition of H322M Tumor Cells Expressing IGF-IR in 3D Culture (Colony Formation Assay)

Figure 3:
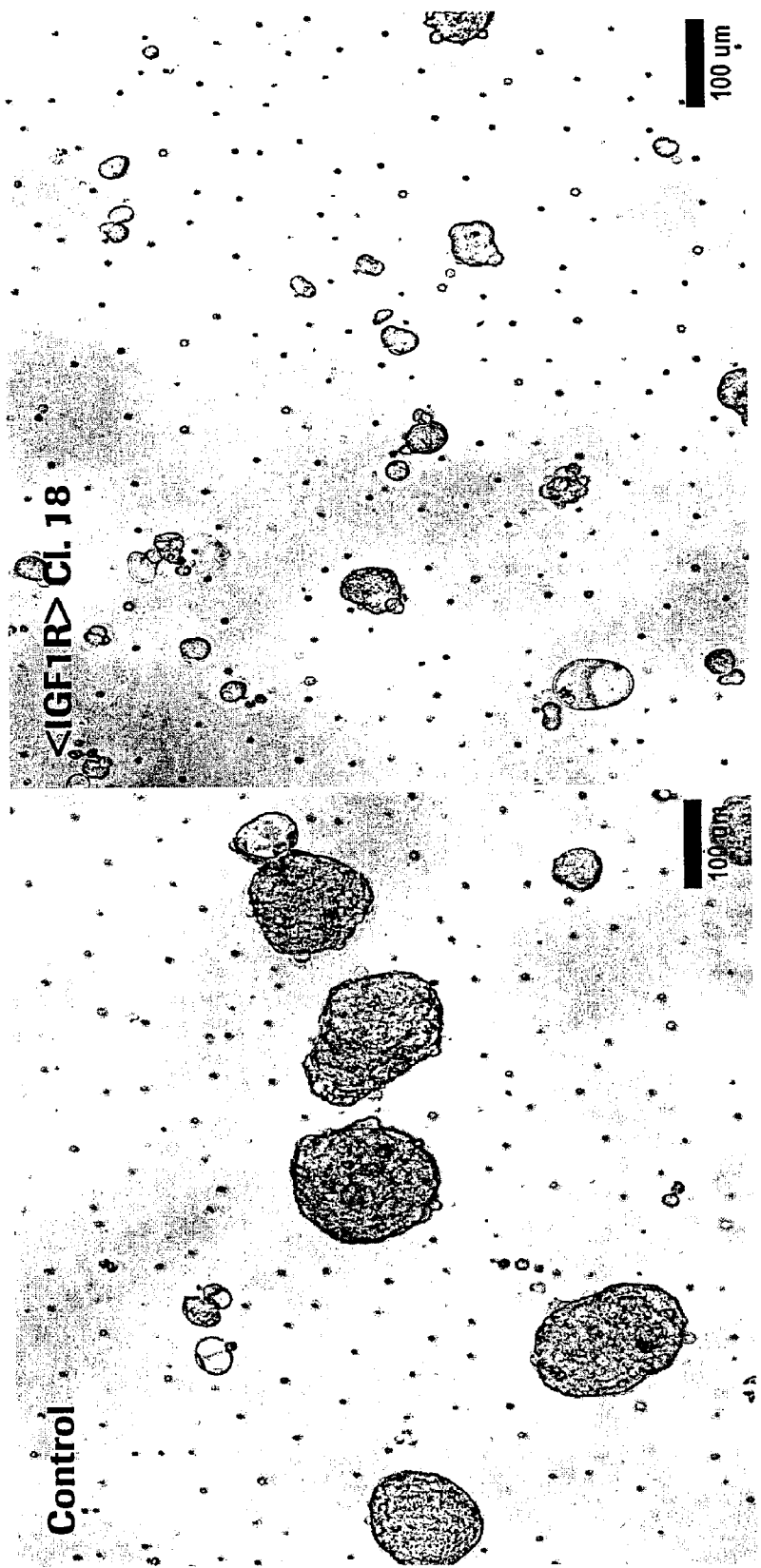
FIG. 3 Colony formation assay for proliferation inhibition in 3D culture (microscopic picture).

H322M cells were cultured in RPMI1640/10% NCS media on poly-HEMA coated dishes to prevent adherence to the plastic surface. Under these conditions H322M cells form dense spheroids that grow three dimensionally (a property that is called anchorage independence). These spheroids represent the three dimensional histoarchitecture and organization of solid tumors in situ. Spheroid cultures were incubated for 5-10 days in the presence of increasing amounts of antibodies from 0-7.5 µg/ml. <HBV> monoclonal antibody was used as neg. control. Colonies were imaged on an inverted microscope (Zeiss Axiovert) using phase contrast and counted using an automated imaging system (MetaMorph). When H322M spheroid cultures were treated with different concentrations (0.5-7.5 µg/ml) of antibody 18, a dose dependent inhibition in growth could be observed, while the control antibody <HBV> had little or no effect. Both the number and the size of colonies was clearly reduced in cultures treated with 7.5 µg/ml of antibody 18 (FIG. 3).

Figure 4:
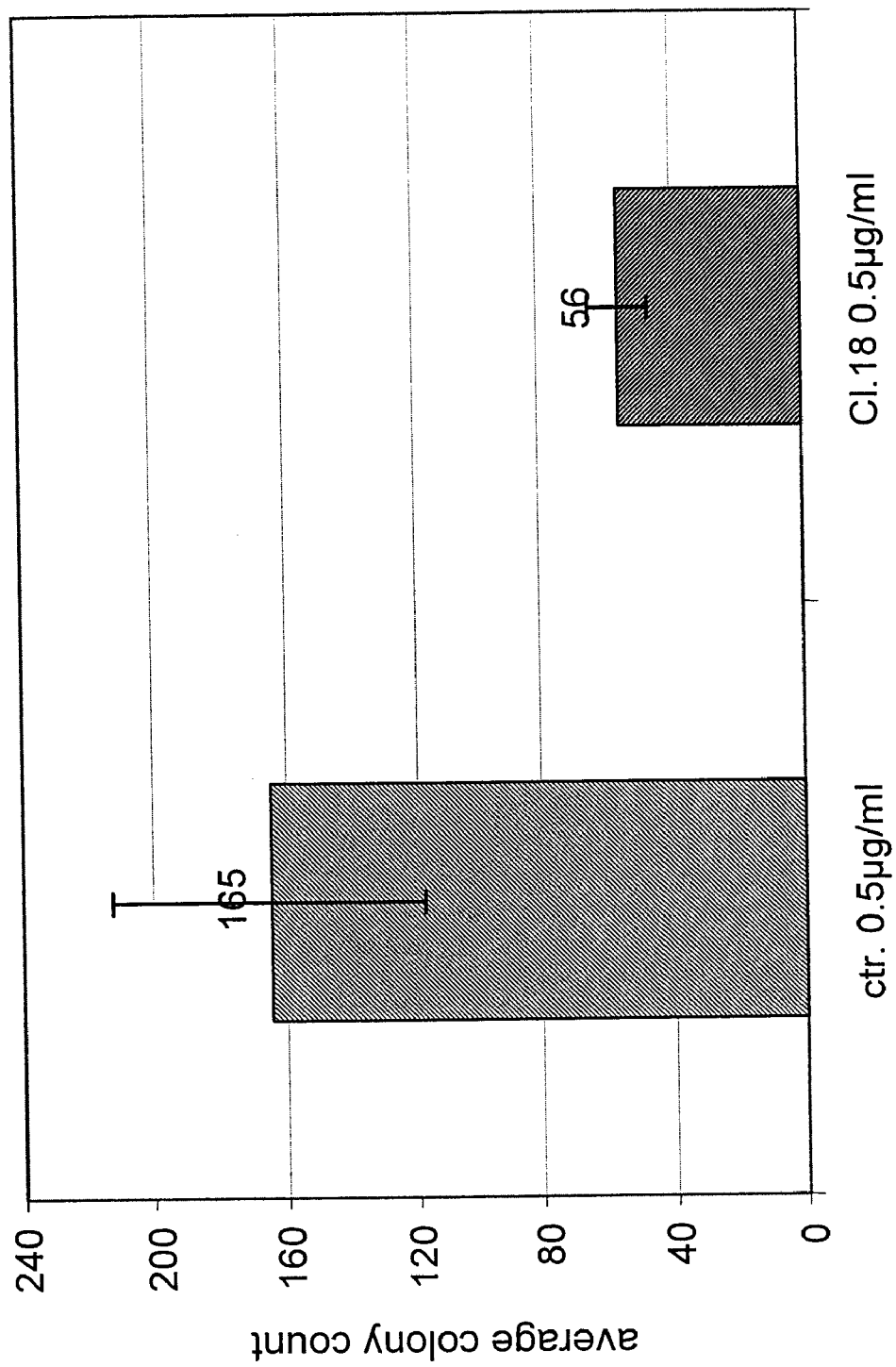
FIG. 4 Colony formation assay for proliferation inhibition in 3D culture (quantification). ctr=control; Cl 18=antibody 18.

Quantitative analysis of colonies larger than 100 µm in diameter revealed that the number of colonies was reduced about 66% in cultures treated with 0.5 µg/ml of antibody 18 (FIG. 4).

EXAMPLE 6

Inhibition of IGF-I and IGF-II Binding to Tumor Cells Expressing IGF-IR

In order to determine the ability of the antibody of the invention to block binding of the ligands IGF-I and IGF-II to the IGF-I receptor (IGF-IR), competition experiments with radioactively labeled ligand peptides were performed.

Human tumor cells (HT29, NCI H322M, 0.5 to $1 \times 10^5$/ml) were plated in RPMI 1640 medium (PAA, Cat. No. E15-039) supplemented with 2 mM L-Glutamin, 1× non-essential amino acids (Gibco, Cat. No. 11140-035), 1 mM sodium pyruvate (Gibco, Cat. No. 11360-039) and 10% heat inactivated FCS (PAA, Cat. No. A15-771). Six bottles in the T175 format were inoculated with 20 ml cells in the respective medium for each experiment and cultivated for two days at 37° C. and 5% $CO_2$ to obtain confluent cell monolayers.

To collect individual cells, 2 ml of 1× Trypsin/EDTA (Gibco, Cat. No. 25300-054) per T175 flask were added and detachment of cells monitored with a Zeiss Axiovert25 microscope. The cells were collected and medium with 10% FCS as described before was added to a total volume of 50 ml. Cells were reisolated by centrifugation for 10 minutes at 1000 rpm (Heraeus sepatech, Omnifuge 2.0 RS) and resuspended in 50 ml of binding buffer (120 mM NaCl, 5 mM KCl, 1.2 mM $MgSO_4$, 1 mM EDTA, 10 mM D(+)glucose, 15 mM NaAc, 100 mM Hepes pH 7.6, 1% BSA). Cells were counted, reisolated by centrifugation and adjusted with binding buffer to $1 \times 10^6$ cells/ml.

$I^{125}$-labeled IGF-I and IGF-II peptides (Amersham, ~2000 Ci/mmol, Cat. No. IM172 and IM238), solubilized in 0.1% $CH_3COOH$, were diluted in binding buffer to a final activity of $4 \times 10^5$ counts/(minute×ml). 75 µl of antibody at the specified concentrations together with 25 µl of prediluted $I^{125}$-labeled IGF-I or IGF-II peptide was added to 200 µl of cell suspension and incubated for 3.5 h at 4° C. Cells were reisolated by centrifugation for 5 minutes at 2000 rpm (Eppendorf, 5415C) and supernatant removed. After washing two times in 1 ml binding buffer, cells were resuspended in 1 ml binding buffer and transferred to scintillation tubes. The amount of radioactive peptide bound to the cell surface receptors was measured on a scintillation counter.

Figure 5:
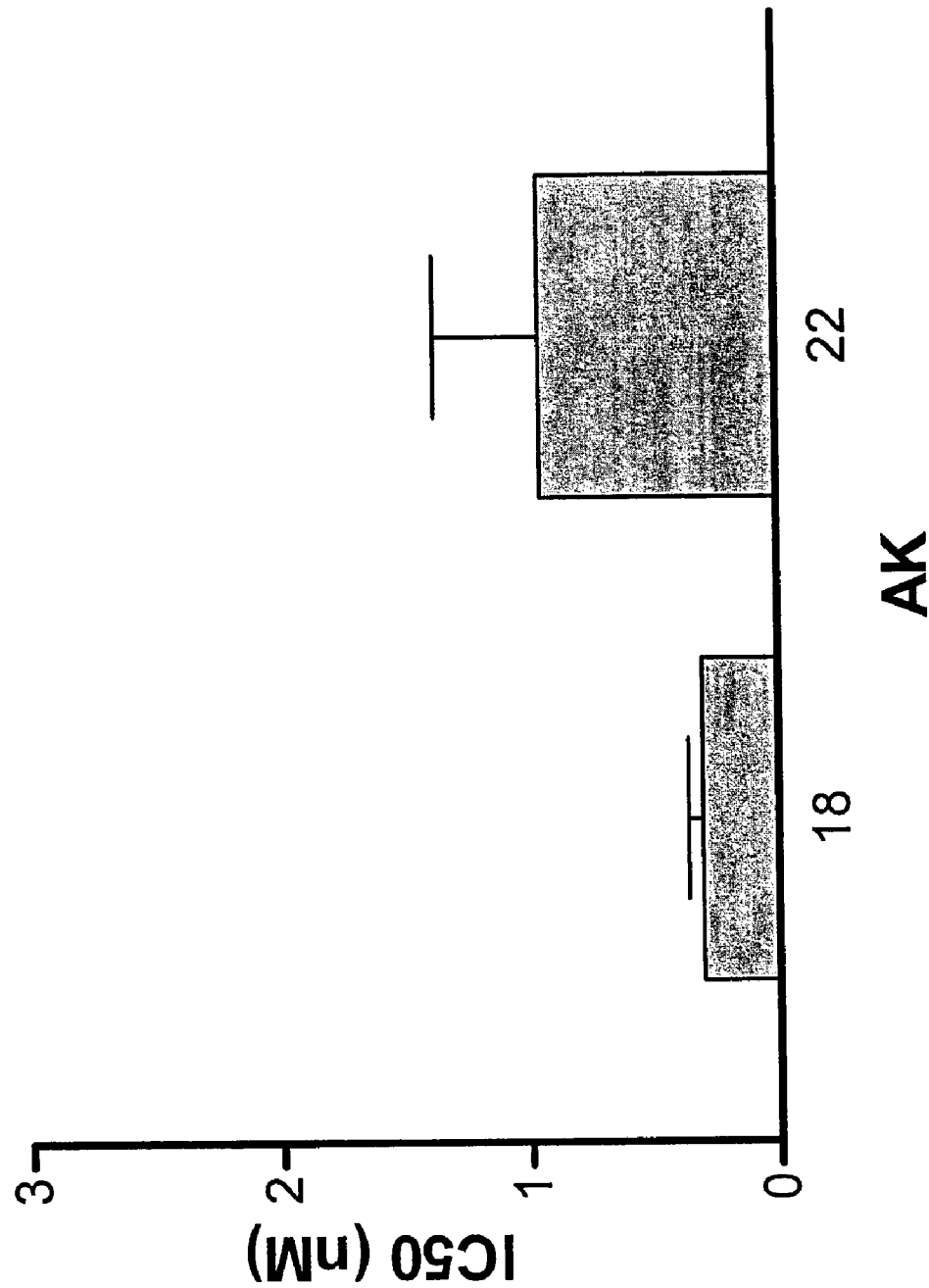
FIG. 5 Inhibition of $I^{125}$-IGF-I binding to HT29 cells by antibodies 18 and 22 ($IC_{50}$ values).
Figure 7:
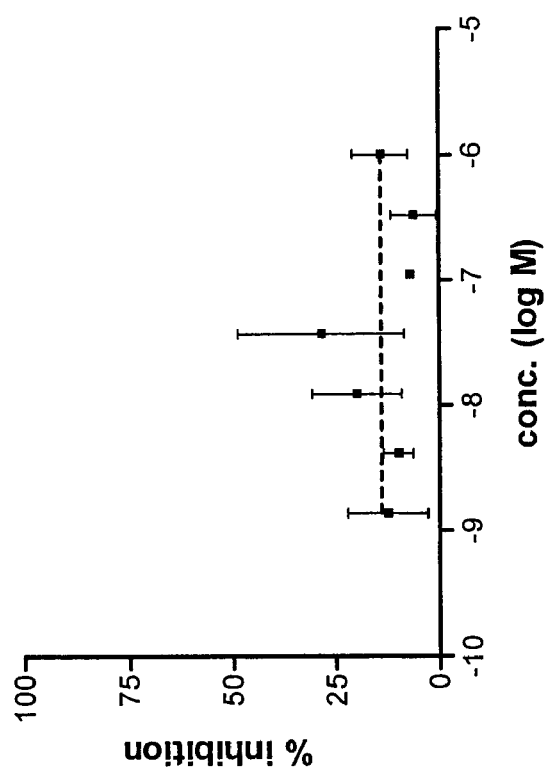
FIG. 7 Inhibition of $I^{125}$-IGF-II binding to HT29 cells by antibody αIR3.
Figure 6:
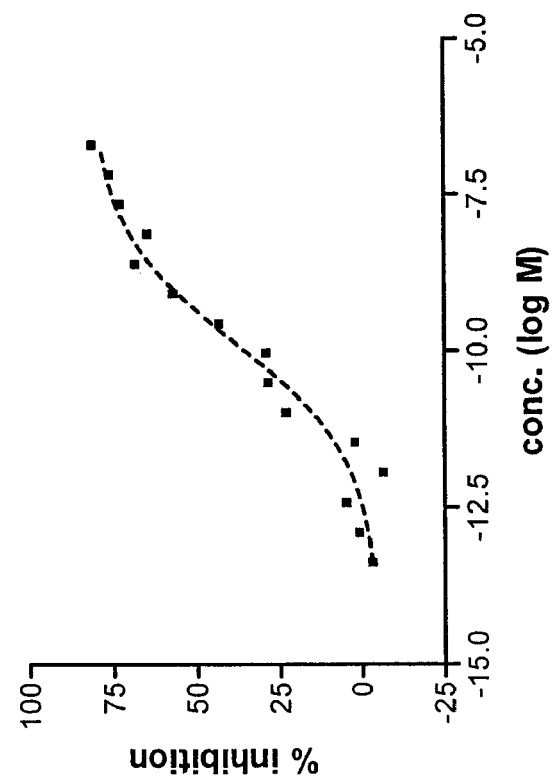
FIG. 6 Inhibition of $I^{125}$-IGF-II binding to HT29 cells by antibody 18.

The resulting $IC_{50}$ curves demonstrating the ability of the antibody to inhibit binding of IGF-I and IGF-II peptide to the IGF-I receptor are shown in FIGS. 5 and 6. The average $IC_{50}$ value for antibody 18 is 0.3 nM. The results for antibody αIR3 are shown in FIG. 7. No detectable inhibition for IGF-II binding could be observed.

EXAMPLE 7

Antibody Competition Assay for IGF-IR Binding

For an epitope mapping of anti-IGF-IR monoclonal antibodies a similar format as for affinity measurement (Example 2) was selected, but IGF-IR was pre-incubated for at least 0.5 hours at RT with the antibody in solution. This mixture was injected and IGF-IR binding (or inhibition) was detected. This assay allows measuring the reciprocal inhibitory activity of monoclonal antibodies for IGF-IR binding. It was found that the antibodies of the invention compete for binding to IGF-IR with αIR3, an antibody which is known to bind to aa 217-274 (Gustafson, T. A., and Rutter, W. J., J. Biol. Chem. 265 (1990) 18663-18667).

EXAMPLE 8

Inhibition of IGF-I Mediated Phosphorylation of IGF-IR and Akt/PKB

In order to determine the ability of the antibody of the invention to inhibit activation and phosphorylation of the IGF-I receptor (IGF-IR), competition experiments were performed with IGF-I peptide and subsequent Western blotting analysis with antibodies specific for phosphorylated tyrosine.

Human tumor cells (HT29, NCI H322M, $5\times10^4$/ml) were plated in RPMI 1640 medium (PAA, Cat. No. E15-039) supplemented with 2 mM L-Glutamin, 1× non-essential aminoacids (Gibco, Cat. No. 11140-035), 1 mM sodium pyruvate (Gibco, Cat. No. 11360-039) and 0.5% heat inactivated FCS (PAA, Cat. No. A15-771). For determination of $IC_{50}$ values, 12 well plates were inoculated with 1 ml cells in the respective medium for each experiment and cultivated for two days at 37° C. and 5% $CO_2$.

After 48 hours of cultivation with low serum medium, the medium was carefully removed and replaced by different concentrations of antibody diluted in the respective medium. After 5 minutes incubation at 37° C. and 5% $CO_2$ IGF-I peptide was added at a final concentration of 2 nM and cells were again incubated for 10 minutes under the conditions mentioned above. The medium was carefully removed by aspiration and 100 μl of cold lysis buffer was added per well (50 mM Hepes pH 7.2, 150 mM NaCl, 1 mM EGTA, 10% glycerol, 1% Triton®-X100, 100 mM NaF, 10 mM $Na_4P_2O_7$, Complete® protease inhibitor). The cells were detached using a cell scraper (Corning, Cat. No. 3010) and well contents transferred to Eppendorf reaction tubes. Cell fragments were removed by centrifugation for 10 minutes at 13000 rpm and 4° C. and half of the supernatant was added to 2× Laemmli sample buffer in a 1:1 (v/v) ratio. For immunoprecipitation of IGF-IR, the remaining supernatant of cell lysates underwent a clarifying spin (10 minutes at 13000 rpm and 4° C.) right before 1 μl of an polyclonal antibody against IGF-IRβ (C-20, Santa Cruz Biotechnologies) or a murine monoclonal antibody (IgG1) which recognizes an epitope within amino acids 440-586 of the extracellular domain (α-chain) of the human IGF Type 1 Receptor was added (mAb 24-55, GroPep). After 2 hours incubation at 4° C. in a rotating Eppendorf reaction tube, 25 μl Protein G Sepharose® beads (Amersham Biosciences, Cat. No. 17-0618-01) were added followed by another incubation step of 1 hour at 4° C. The beads with bound antibody-protein-complexes were isolated by centrifugation (1 minute at 2000 rpm and 4° C.) and washed three times with wash buffer (lysis buffer with only 0.1% Triton®-X100). After boiling the beads in Laemmli sample buffer, cellular proteins were separated by SDS-PAGE and transferred to a nitrocellulose membrane (PROTRAN® BA 85, Schleicher & Schuell) by semi-dry Western blotting.

A phosphotyrosine specific antibody (Upstate, clone 4G10, Cat. No. 05-321) was used to determine phosphorylation status of immunopurified IGF-IR. For the detection of phosphorylated Akt/PKB an antibody with specificity for phosphorylated Ser473 (Cell Signalling, Cat. No. 9271) was applied.

Figure 8:
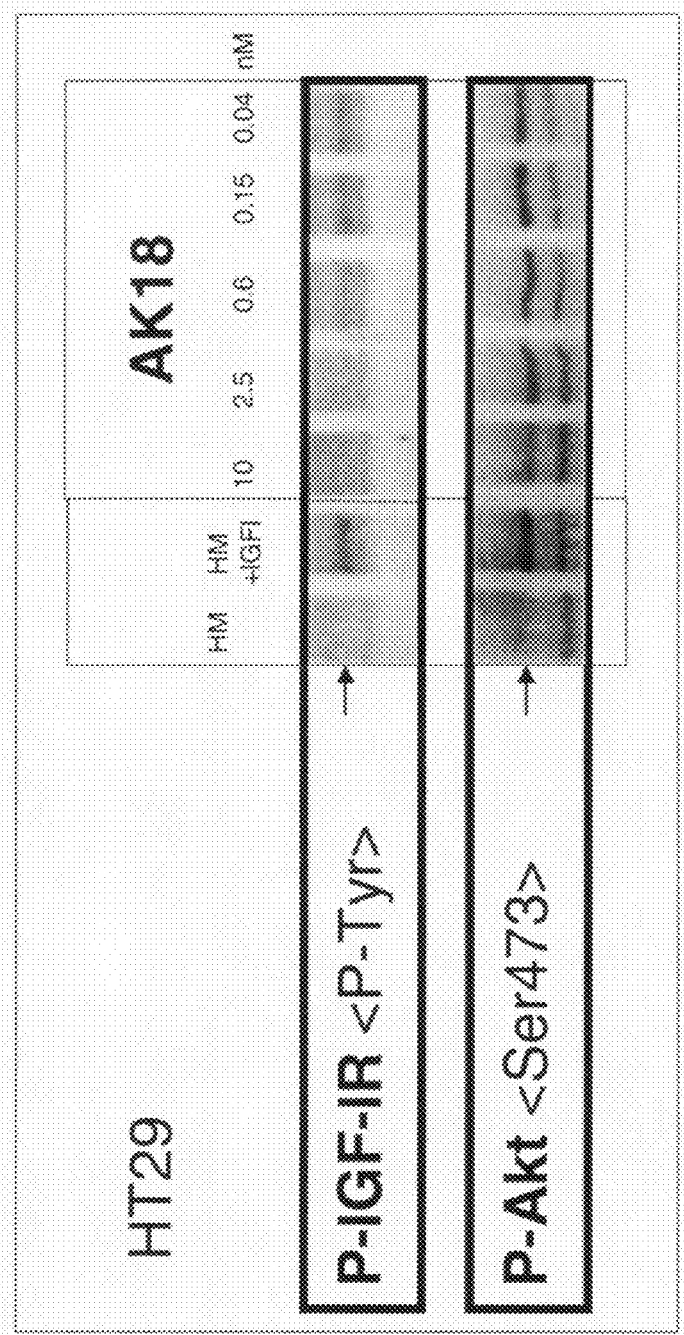
FIG. 8 Blockage of IGF-I induced phosphorylation of both IGF-IR and Akt/PkB.

The observed blockage of IGF-I induced phosphorylation of both IGF-IR and Akt/PKB is shown in FIG. 8.

EXAMPLE 9

Induction of Antibody Mediated Downregulation of IGF-IR In-Vitro

In order to detect effects of the antibody of the invention on the amount of IGF-I receptor (IGF-IR) in tumor cells, time-course experiments and subsequent western-blotting analysis with IGF-IR specific antibodies were performed.

Human tumor cells (HT29, $5\times10^4$ cells/ml) in RPMI 1640 medium (PAA, Cat. No. E15-039) supplemented with 2 mM L-Glutamin, 1× non-essential aminoacids (Gibco, Cat. No. 11140-035), 1 mM sodium pyruvate (Gibco, Cat. No. 11360-039) and 10% heat inactivated FCS (PAA, Cat. No. A15-771). For each incubation period one 12 well plate was inoculated with 1 ml cells in the respective medium for each experiment and cultivated for 24 hours at 37° C. and 5% $CO_2$.

The medium was carefully removed and replaced by different concentrations of antibody diluted in the respective medium. In two control wells, medium was replaced by either medium without antibody or medium with a control antibody (AB-1, Oncogene, Cat. No. GR11). Cells were incubated at 37° C. and 5% $CO_2$ and individual plates were taken out for further processing after 15 minutes, 24 hours and 48 hours.

The medium was carefully removed by aspiration and 100 μl of cold lysis buffer was added per well (50 mM Hepes pH 7.2, 150 mM NaCl, 1 mM EGTA, 10% glycerol, 1% Triton®-X100, 100 mM NaF, 10 mM $Na_4P_2O_7$, Complete® protease inhibitor). The cells were detached using a cell scraper (Corning, Cat. No. 3010) and well contents transferred to Eppendorf reaction tubes. Cell fragments were removed by centrifugation for 10 minutes at 13000 rpm and 4° C. and the supernatant was added to 2× Laemmli sample buffer in a 1:1 (v/v) ratio. Cellular proteins were separated by SDS-PAGE and transferred to a nitrocellulose membrane (PROTRAN® BA 85, Schleicher & Schuell, Cat. No. 10 401196) by semi-dry western-blotting.

An antibody specific for IGF-IR C-20, Santa Cruz Biotechnologies, Cat. No. sc-713) was used to determine protein levels of IGF-IR.

Downregulation of IGF-IR induced by the antibody of the invention after less than 24 hours after addition of the antibody was observed.

EXAMPLE 10

Inhibition of Insulin Binding to 3T3-cells Expressing Human Insulin Receptor

In order to determine whether the antibody of the invention also blocks binding of insulin to the insulin receptor (IR), competition experiments were performed with a radioactively labeled ligand peptide.

3T3 cells ($1\times10^5$/ml) expressing recombinantly high numbers ($>10^5$) human IR were plated in MEM Dulbecco medium (DMEM) with high glucose (PAA, Cat. No. E15-009) supplemented with 2 mM L-Glutamin (Gibco, Cat. No. 25030-024) and 10% heat inactivated FCS (PAA, Cat. No. A15-771). Six bottles in the T175 format were inoculated with 20 ml cells in the respective medium for each experiment and cultivated for two days at 37° C. and 5% $CO_2$ to obtain confluent cell monolayers.

To collect individual cells, 2 ml of 1× Trypsin/EDTA (Gibco, Cat. No. 25300-054) per T175 flask were added and detachment of cells monitored with a microscope. The cells were collected and medium with 10% FCS as described before was added to a total volume of 50 ml. Cells were reisolated by centrifugation for 10 minutes at 1000 rpm and resuspended in 50 ml of binding buffer (120 mM NaCl, 5 mM KCl, 1.2 mM $MgSO_4$, 1 mM EDTA, 10 mM D(+)glucose, 15 mM NaAc, 100 mM Hepes pH 7.6, 1% BSA). Cells were counted, reisolated by centrifugation and adjusted with binding buffer to $1\times10^6$ cells/ml.

$I^{125}$-labeled insulin peptide (Amersham, Cat. No. IM166, ~2000 Ci/mmol), solubilized in 0.1% $CH_3COOH$, were diluted in binding buffer to a final activity of $4*10^5$ counts/(minute*ml). 75 μl of antibody together with 25 μl of prediluted $I^{125}$-labeled insulin peptide was added to 200 μl of cell suspension (final antibody concentration 200 nM) and incubated for 3.5 h at 4° C. Cells were reisolated by centrifugation for 5 minutes at 2000 rpm and supernatant was removed. After washing two times in 1 ml binding buffer, cells were resuspended in 1 ml binding buffer and transferred to scintillation tubes. The amount of radioactive peptide bound to the cell surface receptors was measured on a scintillation counter.

Figure 9:
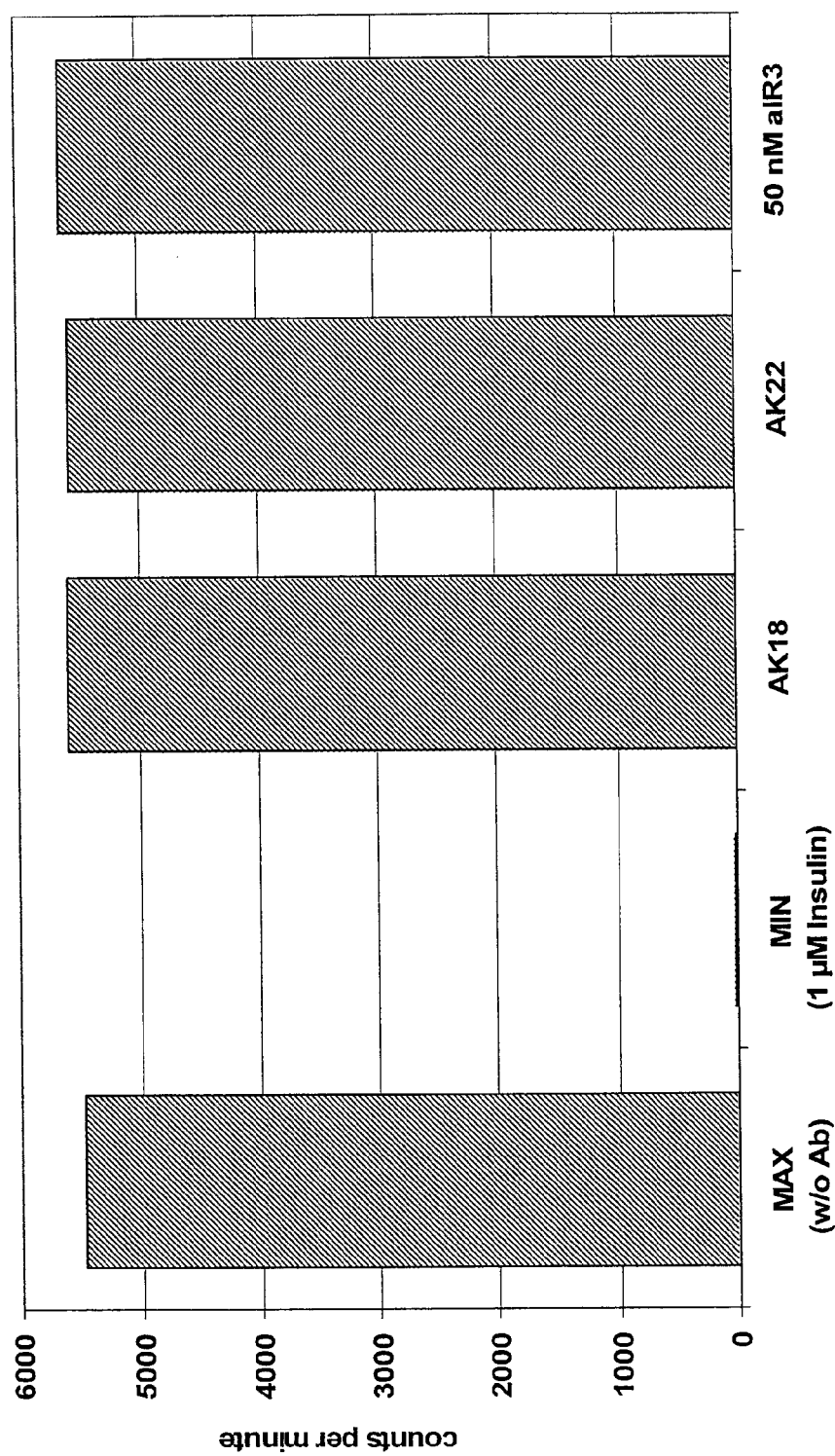
FIG. 9 No inhibition of $I^{125}$-insulin binding to 3T3-IR cells by anti-hIGF-1R antibodies. (MAX w/o Ab: maximal binding of $I^{125}$-insulin; MIN: minimal binding after competition with 1 μM insulin)

The results demonstrate that the antibody of the invention does not interfere with binding of insulin ligand to the insulin receptor (FIG. 9).

EXAMPLE 11

No Stimulation of IGF-IR and Akt/PKB Phosphorylation

In order to exclude IGF-IR stimulating activities of the antibody of the invention, phosphorylation of IGF-IR was determined in the absence of IGF-I ligand but in the presence of the antibody of the invention and a reference antibody (αIR3, Oncogene, Germany). This was performed by a western-blotting analysis with phosphorylation-state specific antibodies. 3T3 cells (ATCC CRL 1658) transfected with IGF-IR ($5*10^4$ cells/ml, Pietrzkowski, Z., et al., Cell Growth Differ. 4 (1992) 199-205) were plated in MEM Dulbecco medium (DMEM) with high glucose (PAA, Cat No. E15-009) supplemented with 2 mM L-Glutamin (Gibco, Cat No. 25030-024) and 0.5% heat inactivated FCS (PAA, Cat No. A15-771) or human tumor cells (HT29, NCI H322M, $5*10^4$/ml) in RPMI 1640 medium (PAA, Cat No. E15-039) supplemented with 2 mM L-Glutamin, 1× non-essential aminoacids (Gibco, Cat No. 11140-035), 1 mM sodium pyruvate (Gibco, Cat No. 11360-039) and 0.5% heat inactivated FCS (PAA, Cat No. A15-771). For determination of $IC_{50}$ values, 12 well plates were inoculated with 1 ml cells in the respective medium for each experiment and cultivated for two days at 37° C. and 5% $CO_2$.

After 48 hours of cultivation with low serum medium, the medium was carefully removed and replaced by different concentrations of antibody diluted in the respective medium. Cells were incubated for 15 minutes under the conditions mentioned above. The medium was carefully removed by aspiration and 100 μl of cold lysis buffer was added per well (50 mM Hepes pH 7.2, 150 mM NaCl, 1 mM EGTA, 10% glycerol, 1% Triton-X100, 100 mM NaF, 10 mM $Na_4P_2O_7$, Complete™ protease inhibitor). The cells were detached using a cell scraper (Corning, Cat No. 3010) and well contents transferred to Eppendorf reaction tubes. Cell fragments were removed by centrifugation for 10 minutes at 13000 rpm and 4° C. (Eppendorf centrifuge 5415R) and half of the supernatant was added to 2× Laemmli sample buffer in a 1:1 (v/v) ratio. For immunoprecipitation of IGF-IR, the remaining supernatant of cell lysates underwent a clarifying spin (10 minutes at 13000 rpm and 4° C.) right before 1 μl of an antibody against IGF-IR was added (C-20, Santa Cruz Biotechnologies, Cat No. sc-713 or mAb 24-55, GroPep, Cat No. MAD1). After 2 hours incubation at 4° C. in a rotating Eppendorf reaction tube, 25 μl Protein G Sepharose™ beads (Amersham Biosciences, Cat No. 17-0618-01) were added followed by another incubation step of 1 hour at 4° C. The beads with bound antibody-protein-complexes were isolated by centrifugation (1 minute at 2000 rpm and 4° C.) and washed three times with wash buffer (lysis buffer with only 0.1% Triton-X100). After boiling the beads in Laemmli sample buffer, cellular proteins were separated by SDS-PAGE and transferred to a nitrocellulose membrane (PROTRAN BA 85, Schleicher & Schuell, Cat No. 10 401196) by semi-dry western-blotting.

A phosphotyrosine specific antibody (Upstate, clone 4G10, Cat No. 05-321, recognizing tyrosine-phosphorylated proteins) was used to determine phosphorylation status of immunopurified IGF-IR. For the detection of phosphorylated Akt/PKB an antibody against Akt1 with specificity for phosphorylated Ser473 (Cell Signalling, Cat No. 9271) was applied.

Figure 10:
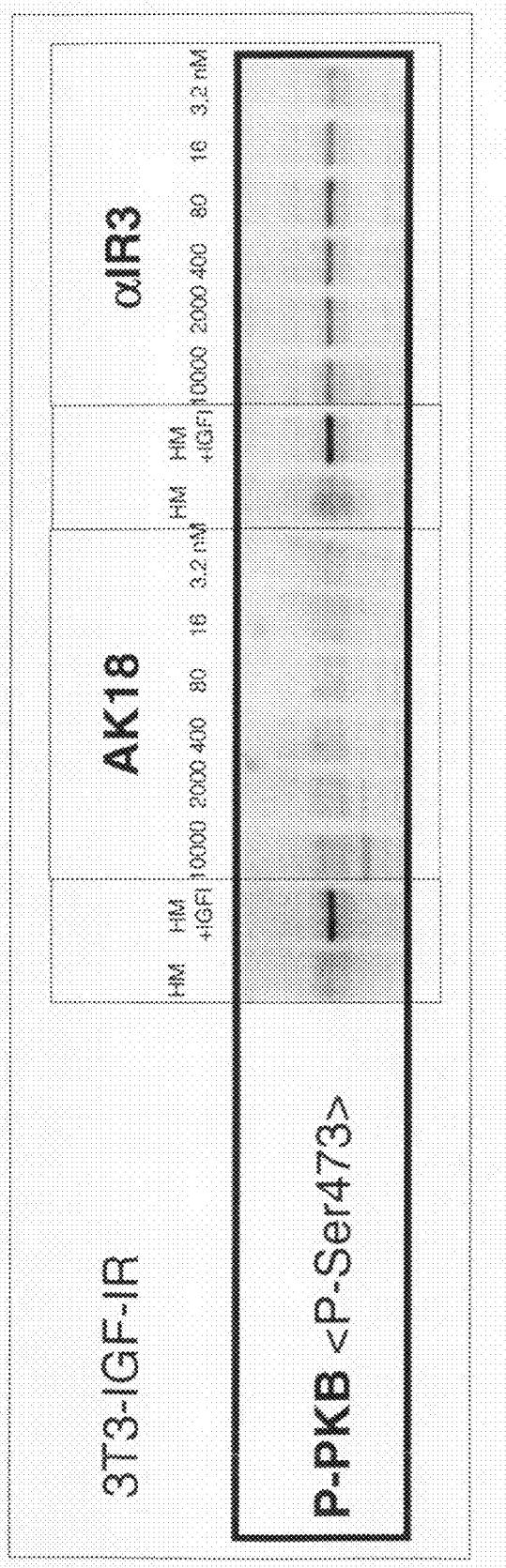
FIG. 10 No stimulating activities of AK18 on IGF-IR overexpressing 3T3 cells.
Figure 11:
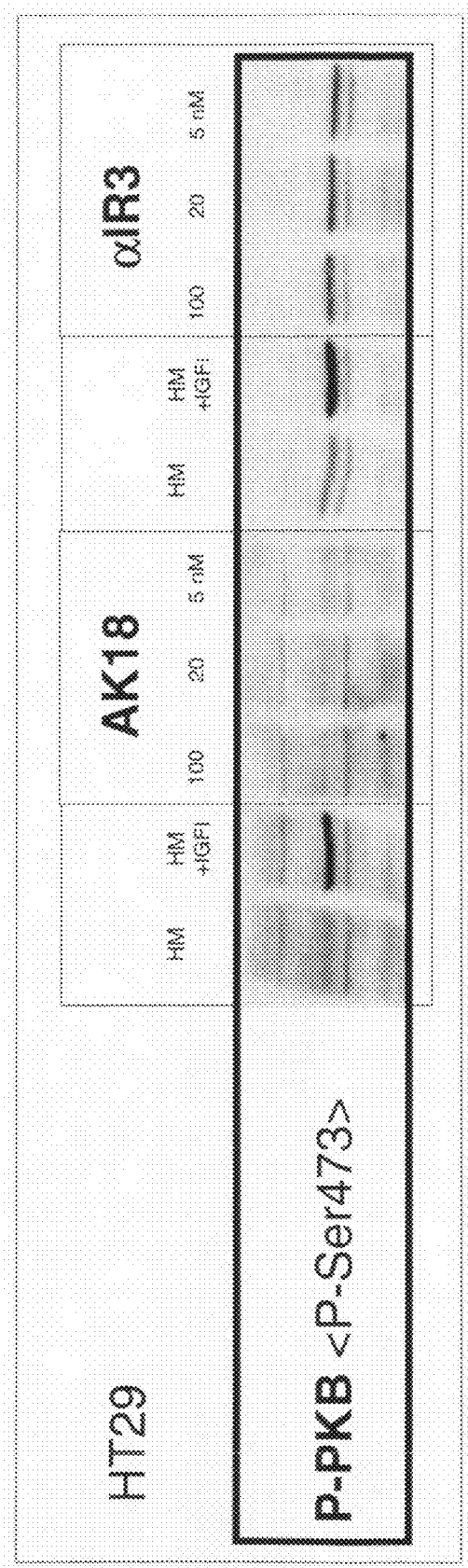
FIG. 11 No stimulating activities of AK18 on human tumor cells (HT29).

It was observed that the Akt/PKB kinase downstream in the signalling pathway of IGF-IR was significantly activated by the reference antibody at concentrations higher than 5 nM but not by the antibody of the invention at concentrations up to 10.000 nM. The results are shown in FIGS. 10 and 11 (HM=low serum medium with 0.5% FCS, HM+IGFI=low serum medium with 0.5% FCS and 10 nM hIGF-I).

EXAMPLE 12

Induction of Receptor Down-regulation in H322M Xenograft Models

Tumors were induced in nude mice and treated once with different concentrations of the antibody of the invention. 24 hours after treatment the tumors were extracted and homogenized under liquid nitrogen. Cold lysis buffer was added (50 mM Hepes pH 7.2, 150 mM NaCl, 1 mM EGTA, 10% glycerol, 1% Triton-X100, 100 mM NaF, 1 mM $Na_3VO_4$, 10 mM $Na_4P_2O_7$, Complete™ protease inhibitor, 1 mM PMSF) in a buffer-volume to tumor-weight ratio of 3:1 and thoroughly mixed with the thawing tumor homogenate. After solubilizing the tissue for 15 minutes on ice, insoluble fragments were removed by centrifugation for 10 minutes at 13000 rpm and 4° C. (Eppendorf centrifuge 5415R). The protein concentration of the samples was determined with the Micro BCA™ Reagents (Pierce) and lysis buffer was added to adjust equal concentrations. Part of the supernatant was added to 2× Laemmli sample buffer in a 1:1 (v/v) ratio. Cellular proteins were separated by SDS-PAGE and transferred to a nitrocellulose membrane (PROTRAN BA 85, Schleicher & Schuell, Cat No. 10 401196) by semi-dry western-blotting. An IGF-IR specific antibody (C-20, Santa Cruz Biotechnologies, Cat No. sc-713) was used to detect IGF-IR.

Upon treatment with the antibody of the invention, we observed a concentration dependent decrease of IGF-IR levels with an estimated EC50 at 0.6 mg/kg (FIG. 12).

EXAMPLE 13

C1q Binding ELISA

Introduction

To determine the ability of antibodies according to the invention to fix C1q an ELISA approach was used. C1q is part of the adaptive immune system and, upon binding to immune complexes, triggers the sequential activation of several zymogens. The enzymes in turn, cause the cleavage of C3 molecules, which can result in the onset of inflammatory reactions, opsonization of foreign or aberrant particles and lysis of cell membranes.

In principle, the ELISA plate is coated with concentration ranges of the antibody, to which human C1q is added. C1q binding is detected by an antibody directed against human C1q followed by a peroxidase-labeled conjugate.

Materials and Methods

Antibody 18, 8 and 23 and control antibodies were tested in concentrations of 10, 5, 1 and 0.5 μg/ml. Table 1 shows the specificities of the samples tested. As a negative control a human IgG4 (CLB, stock 0.5 µg/ml), that binds C1q very weakly, was used. Human IgG1 was incorporated as positive control. Human C1q stock solution with a concentration of 2 µg/ml was used. For the detection of C1q a rabbit antibody directed against C1q (Dako) and an anti-rabbit IgG antibody, conjugated with horseradish peroxidase (Sigma) were used.

Calculations and Curve Fitting

Calculations concerning maximum binding (Bmax) of the HuMAb tested were determined using nonlinear regression curve fitting (one site binding) using Graphpad Prism software.

Results

The antibodies according to the invention show dose dependent binding of human C1q protein. The optical density at 405 nm (OD 405 nm) was plotted against the HuMAb concentrations and the curves were fitted using nonlinear regression. Best fit values for maximum binding (Bmax) are listed in Table 2, as are the correlation coefficient of the curve ($R2$) and the standard deviation for each value. The lowest correlation coefficient had a value of 0.950 (IgG4). With a maximum binding of 0.279, human IgG4 (negative control) shows minimum binding of C1q. Positive controls IgG1 and IgG3 both bind C1q, as shown by a maximum binding of 1.729 and 2.223, respectively.

TABLE 2

Maximum binding (Bmax) of the HuMAb tested in the C1q binding ELISA (n = 3)

| Best fit values | Bmax | Standard deviation Bmax | Goodness of fit $R^2$ | Standard deviation $R^2$ |
| --- | --- | --- | --- | --- |
| IgG1 | 1.729 | 0.166 | 0.983 | 0.010 |
| IgG3 | 2.223 | 0.947 | 0.995 | 0.005 |
| IgG4 | 0.279 | 0.280 | 0.950 | 0.041 |
| Antibody 18 | 1.670 | 0.601 | 0.988 | 0.005 |

The correlation coefficient (R2) and standard deviation and are also listed. Compared to the C1q binding of human IgG4 (negative control, with an O.D. of 0.279), all antibodies tested are equally capable of fixing C1q.

EXAMPLE 14

Determination of Antibody Mediated Effector Functions by Anti-IGF-IR HuMAbs

In order to determine the capacity of the generated HuMAb antibodies to elicit immune effector mechanisms, complement dependent cytotoxicity (CDC) and antibody-dependent cell cytotoxicity (ADCC) studies were performed.

To study CDC (National Cancer Institute, lung adenocarcinoma cell line), H322M, H460 and NIH 3T3 cells ($2-6\times10^6$) were labeled with 100 µCi $^{51}$Cr for 45-120 minutes (Amersham Pharmacia Biotech, UK, Cat CJS11). After labeling the cells were washed twice with 40 ml PBS and spun for 3 minutes at 1500 rpm. The cells were then plated 5,000 per well in a round bottom plate, in a volume of 50 µl. Antibodies were added at a final concentration ranging from 25-0.1 µg/ml in a volume of 50 µl cell culture medium to 50 µl cell suspension and incubated for 30-60 minutes. After incubation excess antibody was removed by washing twice with PBS. 100 µl of active or inactive (30 minutes at 56° C.) pooled human serum, guinea pig, rabbit or nude mice serum diluted between 1/3-1/30 was added, and the cells were incubated for 3 hours, after which the cells were spun down at 1500 rpm for 3 minutes. 100 µl of the supernatant was harvested, transferred to polypropylene tubes and counted in a γ-counter.

To study the effects of the antibodies in ADCC, H322M, H460 and NIH 3T3 or other suitable IGF-IR expressing cells ($2-6\times10^6$) were labeled with 100 µCi $^{51}$Cr for 45-120 minutes (Amersham Pharmacia Biotech, UK, Cat CJS11), washed twice with 40 ml of PBS and spun for 3 minutes at 1500 rpm. The cells were plated 5,000 per well in a round bottom plate, in a volume of 50 µl. HuMAb antibodies were added at a final concentration ranging from 25-0.1 µg/ml in a volume of 50 µl cell culture medium to 50 µl cell suspension and incubated for 15 minutes. Subsequently, 50 µl of effector cells, freshly isolated PBMC or purified effector cells from buffycoats, were added at an E:T ratio in the range of from 100:1 to 5:1. The plates were centrifuged for 2 minutes at 500-700 rpm, and incubated overnight at 37° C. After incubation the cells were spun down for 3 minutes at 1500 rpm and 100 µl of supernatant was harvested, transferred to polypropylene tubes and counted in a γ-counter.

The magnitude of cell lysis by CDC or ADCC is expressed as % of the maximum release of radioactivity from the target cells lysed by detergent corrected for spontaneous release of radioactivity from the respective target cells.

EXAMPLE 15

Growth Inhibition of H322M Tumors

Figure 13:
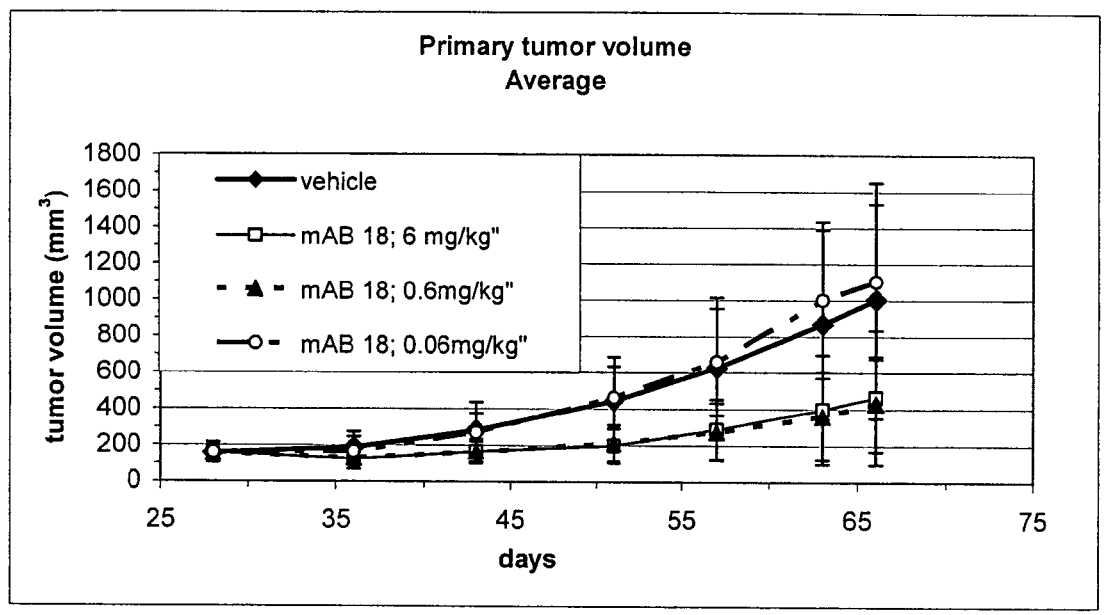
FIG. 13 Treatment with AK18, primary tumor volume

The effects of antibody 18 in vivo was investigated by inducing tumors in athymic nude mice according to established methods. Human H322M NSCLC cells were coinjected together with Matrigel subcutaneously into 6-7 week-old athymic nu mice (nu/nu). For that purpose, $5\times10^6$ H322M cells were concentrated in 100 µl culture medium and mixed with 100 µl Matrigel. 200 µl of this mixture were injected into the right flanks of the mice. Tumor volume was calculated by measuring tumor diameters with Vernier calipers twice a week according to the formula first published by Geran et al. ("Protocols for screening chemical agents and natural products against animal tumors and other biological systems", Cancer Chemother. Rep. 11.301, 1972) where tumor volume [mg]=(length×(width)$^2$). Antibody was administered intraperitoneally (i.p.) at 10 ml/kg. Treatment was started with doubled doses of the antibody administered in doubled volumes. Tumors were induced in nude mice as described above. After tumors had grown to an average volume of 160 mg, mice were treated intraperitoneally six times once a week with 6, 0.6 and 0.06 mg/kg of antibody as consecutive doses starting with 12, 1.2 and 0.12 mg/kg as loading dose given once on the first day of treatment. FIG. 13 pictures the tumor volumes measured during treatment until day 67, when the animals were sacrificed and the experiment was terminated. The experiment demonstrates that blocking of the IGF-IR axis by rhu anti-IGF-IR mAb 18 results in antitumoral efficacy when administered as a single agent at 6 and 0.6 mg/kg. In contrast, 0.06 mg/kg had no effect on tumor growth.

Figure 14:
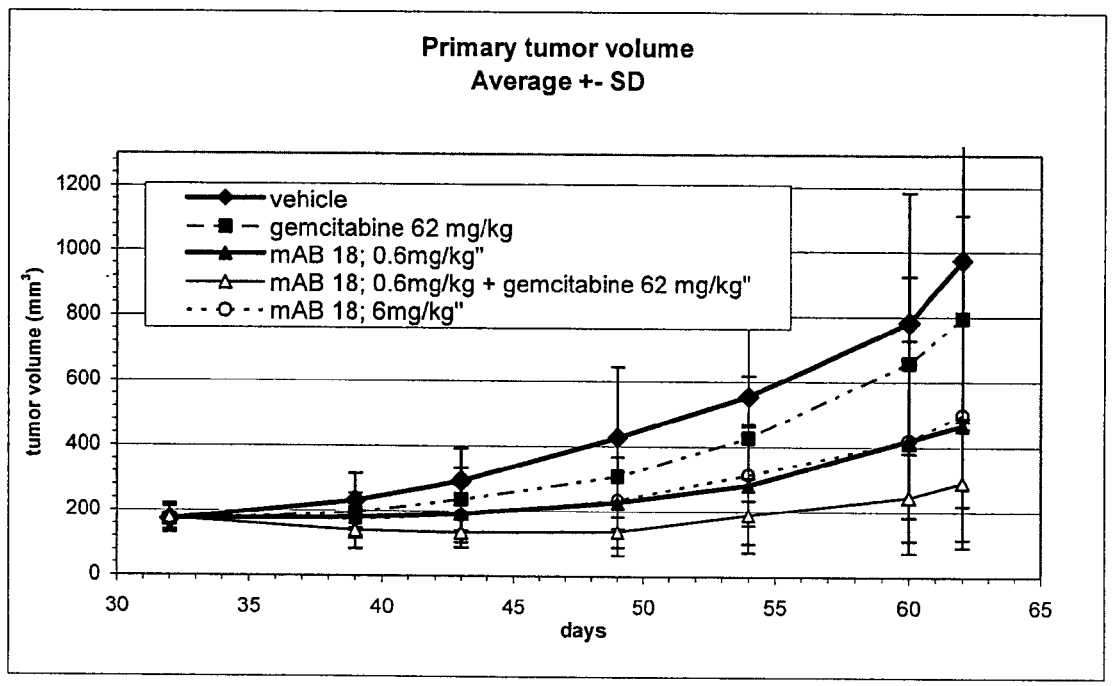
FIG. 14 Treatment with AK18 with or without gemcitabine

In addition antibody 18 was tested in combination with gemcitabine in the same model. Tumors were induced as described above and treatment was initiated when tumors had established and grown to 170 mm$^3$ average in all groups. Antibody was administered once a week i.p. at 6 and 0.6 mg/kg and in combination with 62 mg/kg of gemcitabine at 0.6 mg. Gemcitabine was administered one cycle i.e. every third day for four times in total. Again, treatment was started by administering doubled doses of the antibody. FIG. 14 shows the tumor size in relation to the various treatments over time. The experiment demonstrated that treatment with antibody 18 administered once every seven days inhibits tumor growth by itself and enhances the effectiveness of gemcitabine, a known antimetabolic compound.

EXAMPLE 16

Growth Inhibition of 3T3 Tumors

Figure 15:
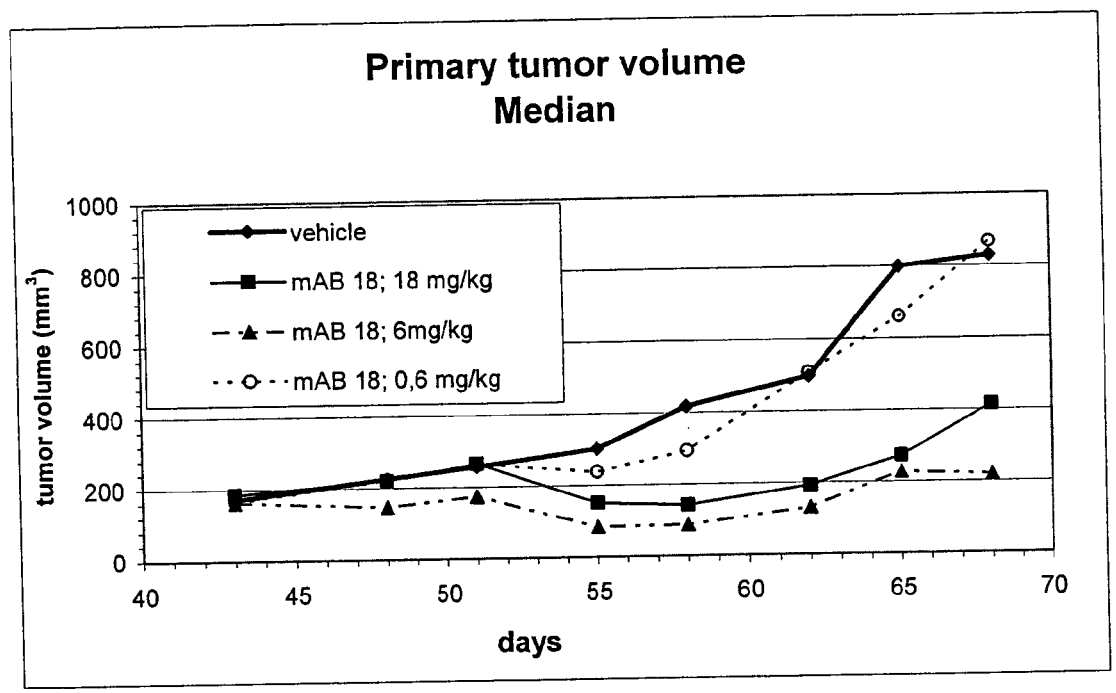
FIG. 15 Treatment with AK18, primary tumor volume

Tumors were induced in nude mice essentially as described in Example 15 except that murine 3T3 fibroblasts overexpressing the human IGF-IR were used. Mice with established tumors of approximately 180 mg were treated intraperitoneally once weekly for seven times with 18, 6 or 0.6 mg/kg of antibody 18. Again, treatment was started with doubled doses of antibody given as loading dose (36, 12 and 1.2 mg/kg). The experiment demonstrates that by treatment with the antibody, tumor growth can be delayed when administered at 18 and 6 mg/kg once weekly (FIG. 15).

LIST OF REFERENCES

Adams, T. E., et al., Cell. Mol. Life Sci. 57 (2000) 1050-1063
Aplin, J. D., and Wriston, J. C. Jr., CRC Crit. Rev. Biochem. (1981) 259-306
Arteaga, C. L., et al., Breast Cancer Res. Treatment 22 (1992) 101-106
Ausubel, F., et al., ed. Current Protocols in Molecular Biology, Greene Publishing and Wiley Interscience, New York (1987)
Barnes, L. M., et al., Biotech. Bioeng. 73 (2001) 261-270
Barnes, L. M., et al., Cytotechnology 32 (2000) 109-123
Benini, S., et al., Clin. Cancer Res. 7 (2001) 1790-1797
Berge, S. M., et al., J. Pharm. Sci. 66 (1977) 1-19
Bergmann, U., et al., Cancer Res. 55 (1995) 2007-2011
Brüggemann, M., et al., J. Exp. Med. 166 (1987) 1351-1361
Brunetti, A., et al., Biochem. Biophys. Res. Commun. 165 (1989) 212-218
Carter, P., et al., Proc. Natl. Acad. Sci. USA 89 (1992) 4285-4289
Chen, J., et al., EMBO J. 12 (1993) 821-830
Chen, J., et al., International Immunology 5 (1993) 647-656
Delafontaine, P., et al., J. Mol. Cell. Cardiol. 26 (1994) 1659-1673
Dricu, A., et al., Glycobiology 9 (1999) 571-579
Durocher, Y., et al., Nucl. Acids. Res. 30 (2002) E9
Edge, A. S., et al. Anal. Biochem. 118 (1981) 131-137
Fishwild, D. M., et al., Nat. Biotechnol. 14 (1996) 845-851
Forsayeth, J. R., et al., Proc. Natl. Acad. Sci. USA 84 (1987) 3448-3451
Geisse, S., et al., Protein Expr. Purif. 8 (1996) 271-282
Gustafson, T. A., and Rutter, W. J., J. Biol. Chem. 265 (1990) 18663-18667
Hailey, J., et al., Mol. Cancer Ther. 1 (2002) 1349-1353
Harding, F., and Lonberg, N., Ann. N. Acad. Sci 764 (1995) 536-546
Hoyne, P. A., et al., FEBS Lett. 469 (2000) 57-60
Johnson, G., and Wu, T. T., Nucleic Acids Res. 28 (2000) 214-218
Jones, P., et al., Nature 321 (1986) 522-525
Kabat et al., Sequences of Proteins of Immunological Interest, 5th Ed. Public Health Service, National Institutes of Health, Bethesda, Md. (1991)
Kalebic, T., et al., Cancer Res. 54 (1994) 5531-5534
Kanter-Lewensohn, L., et al., Melanoma Res. 8 (1998) 389-397
Kato, H., et al., J. Biol. Chem. 268 (1993) 2655-2661
Kaufman, R. J., Mol. Biotechnol. 16 (2000) 151-161
Kull, F. C. Jr., et al. J. Biol. Chem. 258 (1983) 6561-6566
Lammers, R., et al., EMBO J. 8 (1989) 1369-1375
LeRoith, D., et al., Endocrin. Rev. 16 (1995) 143-163
Li, S. L., et al., Biochem. Biophys. Res. Commun. 196 (1993) 92-98
Li, S. L., et al., Cancer Immunol. Immunother. 49 (2000) 243-252
Lonberg, N., and Huszar, D., Intern. Rev. Immunol. 25 (1995) 65-93
Lonberg, N., et al., Nature 368 (1994) 856-859
Lonberg, N., Handbook of Experimental Pharmacology 113 (1994) 49-101
Love, T. W., et al., Methods Enzymol. 178 (1989) 515-527
Makrides, S. C., Protein Expr. Purif. 17 (1999) 183-202
Morgan, D. O., and Roth, R. A., Biochemistry 25 (1986) 1364-1371
Morrison, S. L., et al., Proc. Natl. Acad Sci. USA 81 (1984) 6851-6855
Neuberger, M. S., et al., Nature 314 (1985) 268-270
Norderhaug, L., et al., J. Immunol. Methods 204 (1997) 77-87
O'Brien, R. M., et al., EMBO J. 6 (1987) 4003-4010
Orlandi, R., et al., Proc. Natl. Acad. Sci. USA 86 (1989) 3833-3837
Pessino, A., et al., Biochem. Biophys. Res. Commun. 162 (1989) 1236-1243
Pietrzkowski, Z., et al., Cell Growth Differ. 4 (1992) 199-205
Prigent, S. A., et al., J. Biol. Chem. 265 (1990) 9970-9977
Queen, C., et al., Proc. Natl. Acad. Sci. USA 86 (1989) 10029-10033
Riechmann, L., et al., Nature 332 (1988) 323-327
Rohlik, Q. T., et al., Biochem. Biophys. Res. Comm. 149 (1987) 276-281
Schaefer, E. M., et al., J. Biol. Chem. 265 (1990) 13248-13253
Schlaeger, E.-J., and Christensen, K., Cytotechnology 30 (1999) 71-83
Schlaeger, E.-J., J. Immunol. Methods 194 (1996) 191-199
Scotlandi, K., et al., Cancer Gene Ther. 9 (2002) 296-307
Scotlandi, K., et al., Int. J. Cancer 101 (2002) 11-16
Sojahr, H. T., and Bahl, O. P., Arch. Biochem. Biophys. 259 (1987) 52-57
Soos, M. A., et al., Biochem. J. 235 (1986) 199-208
Soos, M. A., et al., J. Biol. Chem. 267 (1992) 12955-12963
Soos, M. A., et al., Proc. Natl. Acad. Sci. USA 86 (1989) 5217-5221
Stella et al., "Prodrugs: A Chemical Approach to Targeted Drug Delivery," Directed Drug Delivery, Borchardt et al., (ed.), pp. 247-267, Humana Press (1985)
Surinya, K. H., et al., J. Biol. Chem. 277 (2002) 16718-16725
Taylor, L., et al., Int. Immunol. 6 (1994) 579-591 Choi, T. K., et al., Nature Genetics 4 (1993) 117-123
Taylor, L., et al., Nucleic Acids Research 20 (1992) 6287-6295
Taylor, R., et al., Biochem. J. 242 (1987) 123-129
Thotakura, N. R., and Bahl, O. P., Meth. Enzymol. 138 (1987) 350-359
Tuaillon, N., et al., Immunol. 152 (1994) 2912-2920
Tuaillon, N., et al., Proc. Natl. Acad. Sci USA 90 (1993) 3720-3724
Tulloch, P. A., et al., J. Struct. Biol. 125 (1999) 11-18
U.S. Pat. No. 4,179,337
U.S. Pat. No. 4,301,144
U.S. Pat. No. 4,487,603
U.S. Pat. No. 4,496,689
U.S. Pat. No. 4,640,835
U.S. Pat. No. 4,670,417
U.S. Pat. No. 4,675,187

U.S. Pat. No. 4,791,192
U.S. Pat. No. 5,202,238
U.S. Pat. No. 5,204,244
U.S. Pat. No. 5,545,806
U.S. Pat. No. 5,545,807
U.S. Pat. No. 5,569,825
U.S. Pat. No. 5,625,126
U.S. Pat. No. 5,633,425
U.S. Pat. No. 5,661,016
U.S. Pat. No. 5,770,429
U.S. Pat. No. 5,789,650
U.S. Pat. No. 5,814,318
U.S. Pat. No. 5,874,299
U.S. Pat. No. 5,877,397
van Dijk, M. A., and van de Winkel, J. G., Curr. Opin. Pharmacol. 5 (2001) 368-374
Vitetta, E. S., et al., Science 238 (1987) 1098-1104
Werner, R. G., Drug Res. 48 (1998) 870-880
Wilman, "Prodrugs in Cancer Chemotherapy" Biochemical Society Transactions, 14, pp. 375-382, 615th Meeting Belfast (1986)
WO 01/14424
WO 02/053596
WO 87/05330
WO 92/03918
WO 92/22645
WO 93/1227
WO 94/11026
WO 94/25585
WO 98/24884

---

What is claimed is:

1. A purified monoclonal antibody that binds to the IGF-IR which comprises
a heavy chain comprising
a first complementarity determining region consisting of amino acids 31 to 35 of said heavy chain having an amino acid sequence consisting of amino acids 31 to 35 of SEQ ID NO:1,
a second complementarity determining region consisting of amino acids 50 to 66 of said heavy chain having an amino acid sequence consisting of amino acids 50 to 66 of SEQ ID NO:1, and
a third complementarity determining region consisting of amino acids 99 to 107 of said heavy chain having an amino acid sequence consisting of amino acids 99 to 107 of SEQ ID NO:1; and
a light chain comprising
a first light chain complementarity determining region consisting of amino acids 24 to 34 of said light chain having an amino acid sequence consisting of amino acids 24 to 34 of SEQ ID NO:2,
a second light chain complementarity determining region consisting of amino acids 50 to 56 of said light chain having an amino acid sequence consisting of amino acids 50 to 56 of SEQ ID NO:2, and
a third light chain complementarity determining region consisting of amino acids 89 to 98 of said light chain having an amino acid sequence consisting of amino acids 89 to 98 of SEQ ID NO:2.

2. A purified monoclonal antibody that binds to the IGF-IR which comprises
a heavy chain comprising
a first complementarity determining region consisting of amino acids 31 to 35 of said heavy chain having an amino acid sequence consisting of amino acids 31 to 35 of SEQ ID NO:3,
a second complementarity determining region consisting of amino acids 50 to 66 of said heavy chain having an amino acid sequence consisting of amino acids 50 to 66 of SEQ ID NO:3, and
a third complementarity determining region consisting of amino acids 99 to 107 of said heavy chain having an amino acid sequence consisting of amino acids 99 to 107 of SEQ ID NO:3; and
a light chain comprising
a first light chain complementarity determining region consisting of amino acids 24 to 34 of said light chain having an amino acid sequence consisting of amino acids 24 to 34 of SEQ ID NO:4,
a second light chain complementarity determining region consisting of amino acids 50 to 56 of said light chain having an amino acid sequence consisting of amino acids 50 to 56 of SEQ ID NO:4, and
a third light chain complementarity determining region consisting of amino acids 89 to 98 of said light chain having an amino acid sequence consisting of amino acids 89 to 98 of SEQ ID NO:4.

3. A purified monoclonal antibody according to claim 1 that binds to the IGF-IR which comprises
a heavy chain comprising SEQ ID NO:1 and
a light chain comprising SEQ ID NO:2.

4. A purified monoclonal antibody according to claim 2 that binds to the IGF-IR which comprises
a heavy chain comprising SEQ ID NO:3 and
a light chain comprising SEQ ID NO:4.

5. An antibody produced from a hybridoma cell line selected from the group consisting of hybridoma cell line <IGF-1R> HUMAB Clone 18 with accession number DSM ACC 2587 and hybridoma cell line <IGF-1R> HUMAB Clone 22 with accession number DSM ACC 2594.

6. A hybridoma cell line selected from the group consisting of hybridoma cell line <IGF-1R> HUMAB Clone 18 with accession number DSM ACC 2587 and hybridoma cell line <IGF-1R> HUMAB Clone 22 with accession number DSM ACC 2594.

* * * * *

UNITED STATES PATENT AND TRADEMARK OFFICE

(12)       CERTIFICATE EXTENDING PATENT TERM
UNDER 35 U.S.C. § 156

| | | | |
|---|---|---|---|
| (68) | PATENT NO. | : | 7,572,897 |
| (45) | ISSUED | : | August 11, 2009 |
| (75) | INVENTOR | : | Graus et al. |
| (73) | PATENT OWNER | : | Hoffman-La Roche Inc. |
| (95) | PRODUCT | : | TEPEZZA® (teprotumumab-trbw) |

This is to certify that an application under 35 U.S.C. § 156 has been filed in the United States Patent and Trademark Office, requesting extension of the term of U.S. Patent No. 7,572,897 based upon the regulatory review of the product TEPEZZA® (teprotumumab-trbw) by the Food and Drug Administration. According to United States Patent and Trademark Office records, the original expiration date of the patent as of the date of issuance of this certificate is November 6, 2024. Because it appears that the requirements of the law have been met, this certificate extends the term of the patent for the period of

(94)                                              1,578 days subject to the payment of maintenance fees as provided by law, with all rights pertaining thereto as provided by 35 U.S.C. § 156.

I have caused the seal of the United States Patent and Trademark Office to be affixed this <u>18th day</u> of <u>October 2023</u>.

Katherine K. Vidal
Under Secretary of Commerce for Intellectual Property and
Director of the United States Patent and Trademark Office